United States Patent
Biljan et al.

(10) Patent No.: US 10,343,993 B2
(45) Date of Patent: Jul. 9, 2019

(54) PROCESSES AND INTERMEDIATES FOR THE PREPARATION OF PIMAVANSERIN

(71) Applicant: Pliva Hrvatska d.o.o., Zagreb (HR)

(72) Inventors: Tomislav Biljan, Krizevci (HR); Jasna Dogan, Zagreb (HR); Leonid Metsger, Levahim (IL); Sara Morasi Pipercic, Novi Marof (HR); Marina Ratkaj, Zagreb (HR); Maja Matanovic Skugor, Zagreb (HR); Yi Wang, Chester Springs, PA (US)

(73) Assignee: Pliva Hrvatska d.o.o., Zagreb (HR)

( * ) Notice: Subject to any disclaimer, the term of this patent is extended or adjusted under 35 U.S.C. 154(b) by 0 days.

(21) Appl. No.: 15/555,092

(22) PCT Filed: Mar. 2, 2016

(86) PCT No.: PCT/US2016/020337
§ 371 (c)(1),
(2) Date: Sep. 1, 2017

(87) PCT Pub. No.: WO2016/141003
PCT Pub. Date: Sep. 9, 2016

(65) Prior Publication Data
US 2018/0037549 A1    Feb. 8, 2018

Related U.S. Application Data

(60) Provisional application No. 62/126,840, filed on Mar. 2, 2015, provisional application No. 62/161,421, filed on May 14, 2015, provisional application No. 62/187,668, filed on Jul. 1, 2015, provisional application No. 62/188,992, filed on Jul. 6, 2015, provisional application No. 62/198,218, filed on Jul. 29, 2015, provisional application No. 62/270,310, filed on Dec. 21, 2015.

(51) Int. Cl.
| | |
|---|---|
| *C07D 211/58* | (2006.01) |
| *C07D 233/60* | (2006.01) |
| *C07C 259/06* | (2006.01) |
| *C07C 269/04* | (2006.01) |
| *C07C 271/48* | (2006.01) |
| *C07D 233/61* | (2006.01) |
| *C07D 273/01* | (2006.01) |

(52) U.S. Cl.
CPC .......... *C07D 211/58* (2013.01); *C07C 259/06* (2013.01); *C07C 269/04* (2013.01); *C07C 271/48* (2013.01); *C07D 233/60* (2013.01); *C07D 233/61* (2013.01); *C07D 273/01* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 3,479,396 A * | 11/1969 | Gillet | C07C 45/46 558/388 |
| 5,200,408 A | 4/1993 | Bru-Magniez et al. | |
| 7,601,740 B2 | 10/2009 | Weiner et al. | |
| 7,790,899 B2 | 9/2010 | Tolf et al. | |
| 7,868,176 B2 | 1/2011 | Thygesen et al. | |

FOREIGN PATENT DOCUMENTS

| | | | | |
|---|---|---|---|---|
| BE | 661226 A | 9/1965 | | |
| JP | 2013-087107 A | 5/2013 | | |
| WO | WO-2012112447 A3 * | 12/2012 | | C07C 259/06 |
| WO | 2014/085362 A1 | 6/2014 | | |

OTHER PUBLICATIONS

Zhao et al., Process Development of a GCS Inhibitor Including Demonstration of Lossen Rearrangement on Kilogram Scale, Org. Process Res. Dev, 19, 5, pp. 576-581, Apr. 2, 2015 (Web).
Velavan et al., AlMe3-Mediated Regio- and Chemoselective Reaction of Indole with Carbamoyl Electrophiles, European Journal of Organic Chemistry, pp. 3148-3157, Apr. 2013.
Padiya et al. Unprecedented "In Water" Imidazole Carbonylation: Paradigm Shift for Preparation of Urea and Carbamate, Organic Letters, vol. 14, No. 11, pp. 2814-2817, Jun. 2012.
Liu et al., Design, Synthesis and Evaluation of 1,2-benzisothiazol-3-one Derivatives as Potent Caspase-3 Inhibitors, vol. 21, Issue 11, pp. 2960-2967, Jun. 2013.
Duspara et al., Synthesis and Reactivity of N-Alkyl Carbamoylimidazoles: Development of N-Methyl Carbamoylimidazole as a Methyl Isocyanate Equivalent, Journal of Organic Chemistry, vol. 77, No. 22, pp. 10362-10368, Nov. 2012.
Dube et al., Carbonyldiimidazole-Mediated Lossen Rearrangement, Organic Letters, vol. 11, No. 24, pp. 5622-5625, Nov. 2009.

(Continued)

*Primary Examiner* — Heidi Reese
(74) *Attorney, Agent, or Firm* — BakerHostetler

(57) ABSTRACT

The present disclosure relates to novel, safe and efficient processes for the synthesis of Pimavanserin and salts thereof, as well as novel intermediates that can be used in these processes.

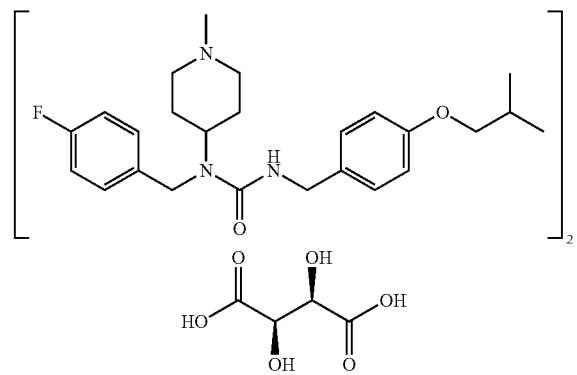

4 Claims, 3 Drawing Sheets

(56) References Cited

OTHER PUBLICATIONS

Akhlaghinia, A New and Convenient Method of Generating Alkyl Isocyanates from Alcohols, Thiols and Trimethylsilyl Ethers Using Triphenylphosphine/2,3-Dichloro-5,6-dicyanobenzoquinone/Bu4NOC, Synthesis, 12, pp. 1955-1958, 2005.

Akhlaghinia et al., A New and Convenient Method of Generating Alkyl Isocyanates from Alcohols, Thiols, and Trimethylsityl Ethers Using a 2,4,5-Trichloro[1,3,5]Triazine/n-Bu4NOCN, Academic Journals, 31, 1, pp. 35-43, 2007.

\* cited by examiner

Crystalline form I of N-(4-fluorobenzyl)-1-methylpiperidin-4-amine dihydrochloride (Compound Vx2 HCl)

Crystalline form II of N-(4-fluorobenzyl)-1-methylpiperidin-4-amine dihydrochloride (Compound Vx2 HCl)

PROCESSES AND INTERMEDIATES FOR THE PREPARATION OF PIMAVANSERIN

CROSS-REFERENCE TO RELATED APPLICATIONS

This application is the National Stage Application of International Patent Application No. PCT/US2016/020337, filed Mar. 2, 2016 which claims the benefit of U.S. Provisional Patent Application Nos. 62/126,840, filed Mar. 2, 2015; 62/161,421, filed May 14, 2015; 62/187,668, filed Jul. 1, 2015; 62/188,992, filed Jul. 6, 2015; 62/198,218, filed Jul. 29, 2015; and 62/270,310, filed Dec. 21, 2015, the entireties of which are incorporated by reference herein.

FIELD OF THE DISCLOSURE

The present disclosure relates to novel, safe and efficient processes for the synthesis of Pimavanserin and salts thereof, as well as novel intermediates that can be used in these processes.

BACKGROUND OF THE DISCLOSURE

Pimavanserin tartrate, 1-(4-fluorobenzyl)-3-(4-isobutoxybenzyl)-1-(1-methylpiperidin-4-yl)urea L-hemi-tartrate, has the following chemical structure:

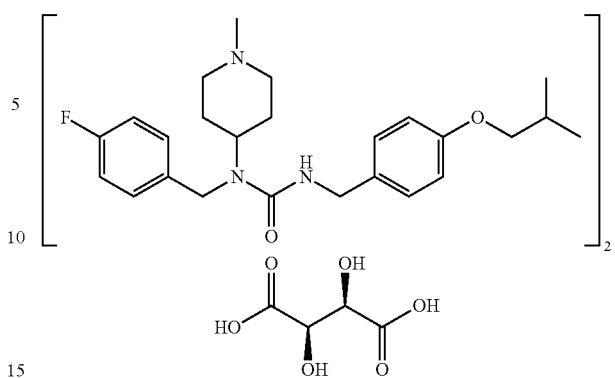

Pimavanserin tartrate was developed by Acadia Pharmaceuticals and was approved under the trade name NUPLAZID® for use in patients with Parkinson's disease psychosis.

Pimavanserin free base and its synthesis are disclosed in U.S. Pat. No. 7,601,740 (referred to herein as US '740 or the '740 patent) and U.S. Pat. No. 7,790,899 (referred to herein as US '899 or the '899 patent). US '740 discloses the synthesis of Pimavanserin free base (also referred to herein as "Compound A"), which includes O-alkylation followed by ester hydrolysis, and then in situ azidation. This process suffers from low process safety, and utilizes the hazardous reagent diphenylphosphoryl azide. The process is illustrated by the following Scheme 1.

Scheme 1:

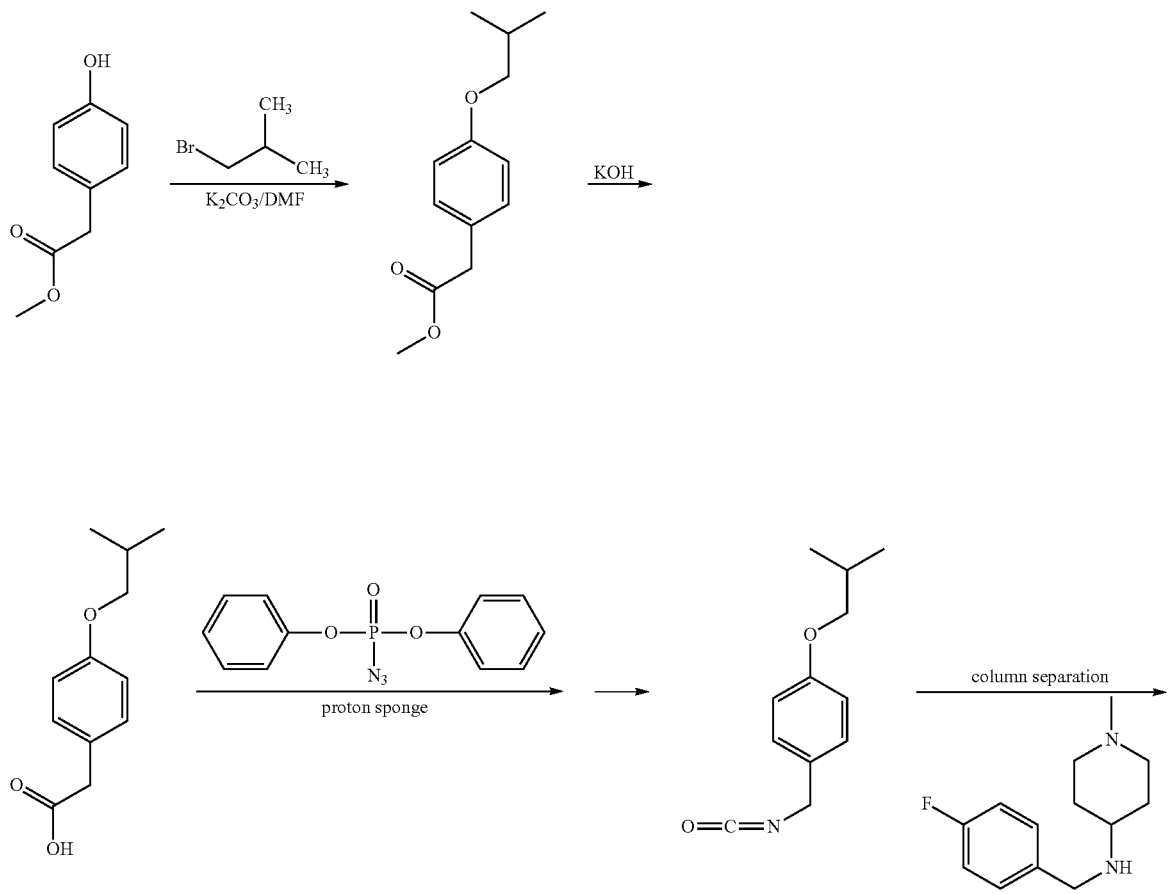

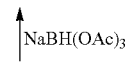
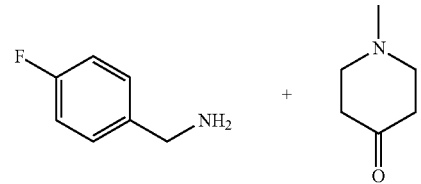
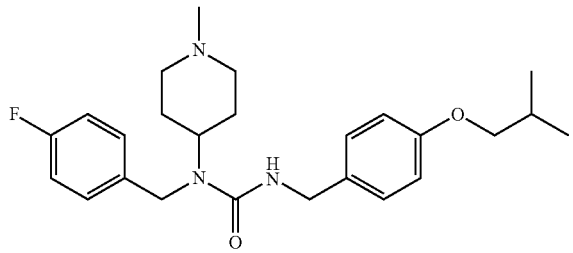
(A)
US '899 describes another process, which includes O-alkylation followed by aldehyde reductive amination to obtain an intermediate which is then reacted with the hazardous reagent phosgene. This process is illustrated by the following Scheme 2:
Scheme 2:
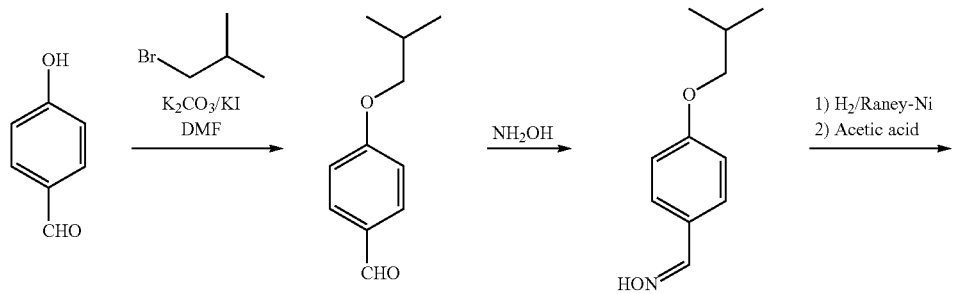
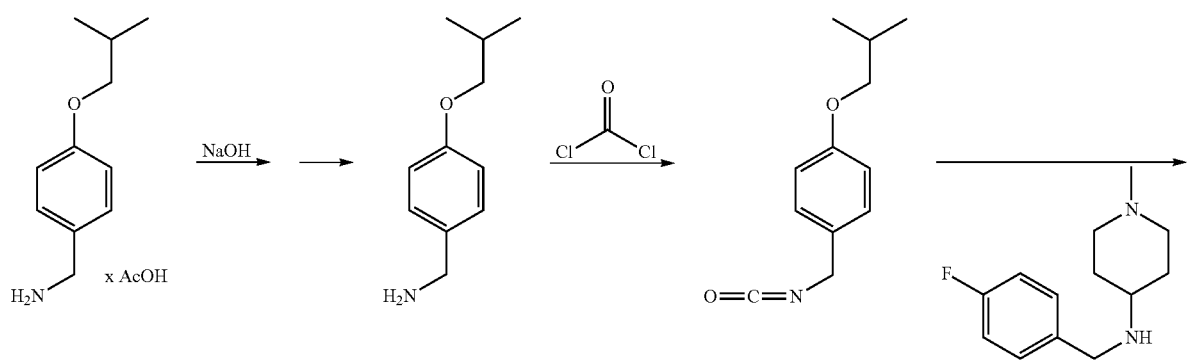

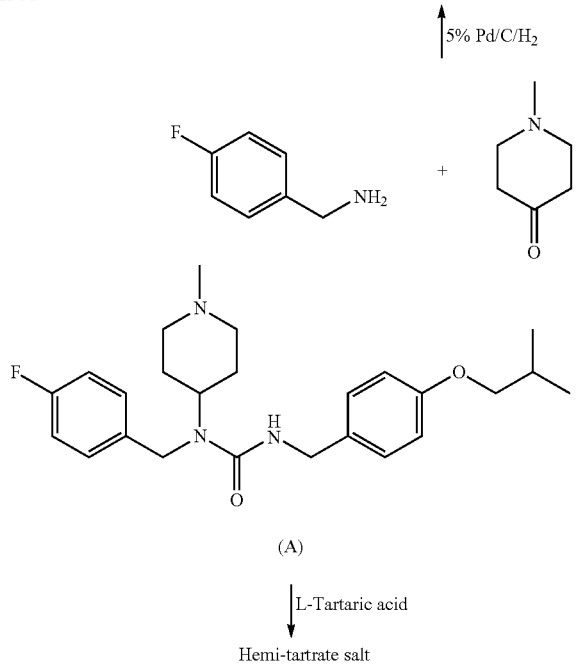

(A)

↓ L-Tartaric acid

Hemi-tartrate salt

Both of the above processes for the preparation of Pimavanserin include a reaction between 1-isobutoxy-4-(isocyanatomethyl)benzene, a benzyl isocyanate intermediate, and N-(4-fluorobenzyl)-1-methylpiperidin-4-amine. Processes for preparing benzyl isocyanate derivatives are generally described in the literature, such as in US '740; US '899; Bioorganic & Medicinal Chemistry, 21(11), 2960-2967, 2013; JP 2013087107; Synthesis (12), 1955-1958, 2005; and Turkish Journal of Chemistry, 31(1), 35-43, 2007. These processes often use the hazardous reagents like phosgene derivatives or diphenylphosphoryl azide.

Accordingly, there is a need for additional processes allowing the efficient and safe synthesis of Pimavanserin.

SUMMARY OF THE DISCLOSURE

The present disclosure relates to novel, safe and efficient processes and intermediates for the synthesis of Pimavanserin and salts thereof. Coupling of carbamate derivatives to amines are typically performed using secondary amines. It was surprisingly found that such a reaction for the preparation of Pimavanserin failed to produce the desired compound, while a reaction with a primary amine intermediate provided the desired compound with great efficiency and quality.

In a first aspect, the present disclosure relates to a process for preparing the compound of formula XVII

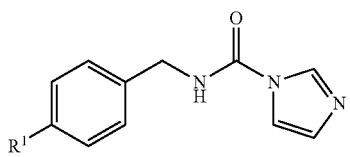

XVII comprising reacting a compound of formula XI-a:

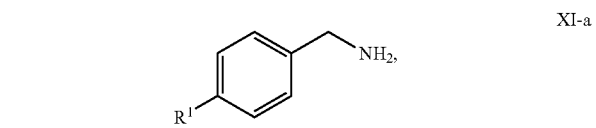

XI-a wherein $R^1$ is a 2-methylpropan-oxy ("isobutoxy") group or a group that can be converted into an isobutoxy group, or a salt thereof, with 1,1'-carbonyldiimidazole (CDI).

In another, related aspect, the present disclosure relates to the compound of formula XVII:

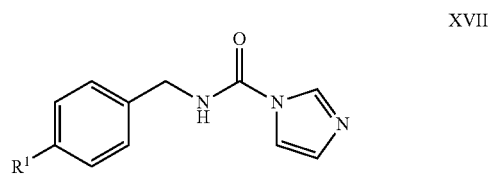

XVII wherein $R^1$ is as defined above. The compound of formula XVII may be employed as a useful intermediate in the synthesis of Pimavanserin or a salt thereof.

The present disclosure also relates to the use of the compound of formula XVII in the preparation of Pimavanserin or a salt thereof.

The present disclosure further provides a process comprising reacting the compound of formula XVII with a compound of formula V.

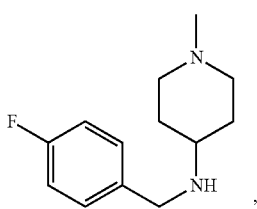

or a salt thereof, to obtain Pimavanserin, or a salt thereof.

In another aspect, the present disclosure provides a process for preparing the compound of formula Z.

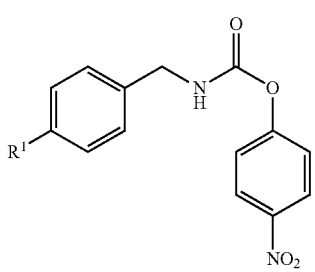

comprising reacting a compound of formula XI-a:

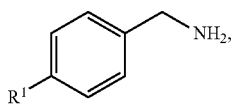

wherein $R^1$ is a 2-methylpropan-oxy ("isobutoxy") group or a group that can be converted into an isobutoxy group, or a salt thereof, with 4-nitrophenyl chloroformate.

The present disclosure also relates to the compound of formula Z:

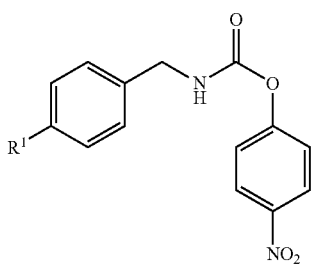

wherein $R^1$ is as defined above. The compound of formula Z may also be employed as a useful intermediate in the synthesis of Pimavanserin or a salt thereof.

The use of said compound of formula Z in the preparation of Pimavanserin, or a salt thereof represents another aspect of the present disclosure.

In a related aspect, the present disclosure provides a process comprising reacting the compound of formula Z with a compound of formula V

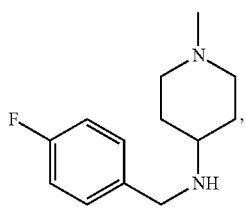

or a salt thereof, to obtain Pimavanserin or salts thereof.

The present disclosure also relates to the compound of the formula XVIII:

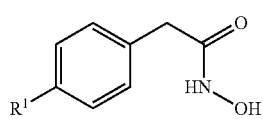

or of formula XIX:

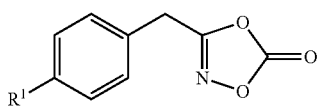

wherein $R^1$ is a 2-methylpropan-oxy ("isobutoxy") group or a group that can be converted into an isobutoxy group. The compounds of formula XVIII and formula XIX, respectively, may likewise be employed as useful intermediates in the synthesis of Pimavanserin or a salt thereof.

Thus, another aspect of the present disclosure relates to the use of the compound of formula XVIII or the compound of formula XIX in the preparation of Pimavanserin or salts thereof.

In yet another, related aspect, the present disclosure relates to a process comprising reacting a compound of formula XVIII

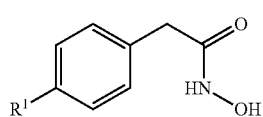

wherein $R^1$ is as defined above, with 1,1'-carbonyldiimidazole (CDI) to obtain a compound of formula XIX

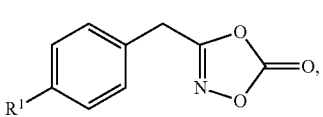

and further reacting the compound of formula XIX with a compound of formula V

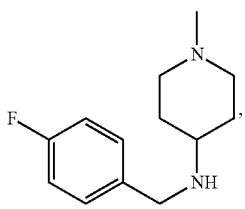

or a salt thereof, to obtain Pimavanserin or a salt thereof.

DETAILED DESCRIPTION OF THE DISCLOSURE

Definitions

Figure 1:
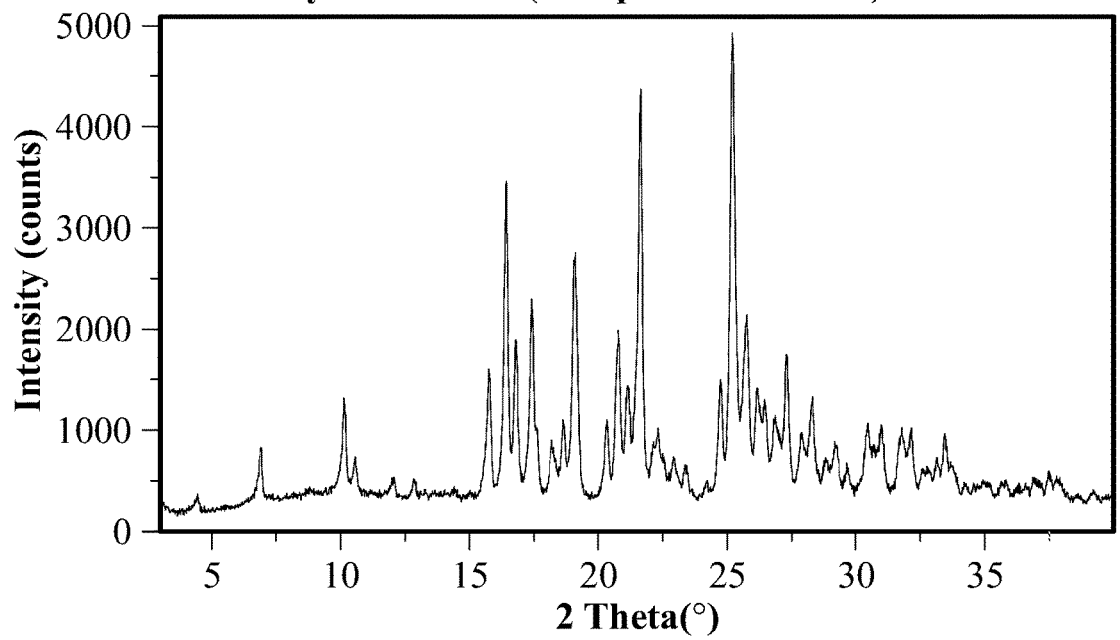
FIG. 1 shows an x-ray powder diffractogram ("PXRD" or "XRPD") of crystalline form I of N-(4-fluorobenzyl)-1-methylpiperidin-4-amine dihydrochloride (Compound V×2 HCl)

As used herein, and unless indicated otherwise, the term "isolated" corresponds to compounds that are physically separated from the reaction mixture in which they are formed.

The processes or steps may be referred to herein as being carried out "overnight." This refers to time intervals, e.g., for the processes or steps, that span the time during the night, when the processes or steps may not be actively observed. The time intervals are from about 8 to about 20 hours, or about 10-18 hours, or about 16 hours.

As used herein, and unless indicated otherwise, the term "reduced pressure" refers to a pressure of about 10 mbar to about 500 mbar, or about 50 mbar.

A thing, e.g., a reaction mixture, may be characterized herein as being at, or allowed to come to "room temperature" or "ambient temperature", often abbreviated as "RT". This means that the temperature of the thing is close to, or the same as that of the space, e.g., the room or fume hood, in which the thing is located. Typically, room temperature is from about 20° C. to about 30° C., or about 22° C. to about 27° C., or about 25° C.

The amount of solvent employed in chemical processes, e.g., reactions or crystallizations, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume.

"Alkyl" refers to a monoradical of a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, sec-butyl, isobutyl, etc. Alkyl groups typically contain 1-10 carbon atoms, such as 1-6 carbon atoms or 1-4 carbon atoms, and can be substituted or unsubstituted.

"Alkyloxy" refers to a linear or branched, hydrocarbon group of formula —O-alkyl, in which the term "alkyl" is defined supra, and may include, e.g., a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

"Aryl" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. An aryl group may contain 6 (i.e., phenyl) or 9 to 15 ring atoms, such as 6 (i.e., phenyl) or 9-11 ring atoms, e.g., 6 (i.e., phenyl), 9 or 10 ring atoms.

"Alkylaryl" refers to an alkyl group in which a hydrogen atom is replaced by an aryl group, wherein alkyl group and aryl group are defined supra. Alkylaryl groups can be substituted or unsubstituted. Examples include, but are not limited to, benzyl ($C_6H_5CH_2$—).

"Alcohol protecting groups" refers to protecting groups which are introduced into a molecule by chemical modification of hydroxyl groups, for example to obtain chemoselectivity in a subsequent reaction. The term and use of protecting groups is well known in the art and for example described in Philipp J. Kocieński: Protecting Groups, 1. Auflage, Georg Thieme Verlag, Stuttgart 1994; Peter G. M. Wuts, Theodora W. Greene: Green's Protective Groups in Organic Synthesis, Fifth Ed. John Wiley & Sons Inc., Hoboken, N.J. Alcohol protecting groups can be for example acetoxy groups, benzoyl groups (Bz), benzyl groups (Bn), β-methoxyethoxymethyl ether (MEM), [bis-(4-methoxyphenyl)phenylmethyl] (DMT), methoxymethyl ether (MOM), [(4-methoxyphenyl)diphenylmethyl, (MMT), p-methoxybenzyl ether (PMB), methylthiomethyl ether, pivaloyl (Piv), tetrahydropyranyl (THP), triphenylmethyl (Tr), silyl ethers, trimethylsilyl ethers (TMS), triethylsilyl ethers (TES), tert-butyldimethylsilyl ethers (TBDMS), tri-iso-propylsilyloxymethyl ethers (TOM), triisopropylsilyl (TIPS) ethers, methyl ethers and ethoxyethyl ethers (EE).

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of a Pimavanserin or Pimavanserin intermediate, such as Compound 1, referred to herein as being characterized by graphical data "as depicted in" or "as substantially depicted in" a Figure will thus be understood to include any crystal forms of Pimavanserin or Pimavanserin intermediate, such as Compound 1, characterized with the graphical data having such small variations, as are well known to the skilled person, in comparison with the Figure.

As used herein, unless stated otherwise, the XRPD measurements were taken using a CuK$_\alpha$ radiation wavelength of 1.54184 Å.

As used herein, and unless indicated otherwise, the terms "wet crystalline form" or "wet form" refer to a polymorph that was not dried using any conventional techniques to remove residual solvent. Examples for such conventional techniques can be, but not limited to, evaporation, vacuum drying, oven drying, drying under nitrogen flow etc.

As used herein, and unless indicated otherwise, the terms "dry crystalline form" or "dry form" refer to a polymorph that was dried using any conventional techniques to remove residual solvent. Examples for such conventional techniques can be, but not limited to, evaporation, vacuum drying, oven drying, drying under nitrogen flow etc.

As used herein, the term "crystalline Pimavanserin form Y", "form alpha" or "Pimavanserin form alpha" refers to the crystalline from alpha as described in U.S. Pat. No. 7,868,176.

The present disclosure provides a number of new intermediates, as well as their uses in processes for preparing Pimavanserin or salts thereof. Pimavanserin is a drug typically used for the treatment of patients with Parkinson's disease psychosis.

Salts of Pimavanserin can for example be formed with an acid wherein the corresponding base is an anion. Exemplary anions include, but are not limited to, tartrate, hemi-tartrate, phosphate, sulphate, nitrate, diphosphate, bicarbonate, carbonate, clavulanate, isothionate, borate, halide, nitrate, acetate, succinate, lactate, lactobionate, laurate, mandelate, malate, citrate, fumarate, maleate, oleate, oxalate, ascorbate, nicotinate, benzoate, mesylate, salicylate, stearate, tannate, tosylate, valerate, methanesulfonate, ethanesulfonate, benzenesulfonate, p-toluensulfonate, 2-ethane disulfonate, or naphthalenesulfonate.

Salts of Pimavanserin are preferably pharmaceutically acceptable salts. The term "pharmaceutically acceptable salt" refers to a salt of a compound that does not cause significant irritation to an organism to which it is administered and does not abrogate the biological activity and properties of the compound. Pharmaceutical acceptable salts can be obtained by reacting Pimavanserin with inorganic acids such as hydrohalic acid (e.g., hydrochloric acid or hydrobromic acid), sulfuric acid, phosphoric acid and the like. Pharmaceutically acceptable salts may also be obtained by reacting a compound with an organic acid such as aliphatic or aromatic carboxylic or sulfonic acids, for example tartaric, acetic, succinic, lactic, malic, tartaric, citric, ascorbic, nicotinic, methanesulfonic, ethanesulfonic, p-toluensulfonic, salicylic or naphthalenesulfonic acid. A particularly preferred salt of Pimavanserin is the hemitartrate salt as this is the currently marketed form of the drug.

The present disclosure also relates to certain compounds useful as intermediates in the synthesis of Pimavanserin. Such intermediates may employed either in their free base (or free acid) form, or in the form of their acid addition salts (in case of a basic group such as an amino group being present), or in the form of their base addition salts (in case an acidic functional group is present), with the possible choices including the examples listed above.

In a first aspect, the present disclosure relates to a process for preparing a compound of the following formula XVII.

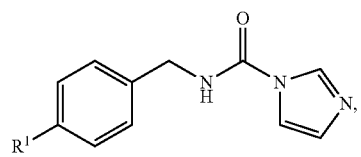

wherein said process comprises reacting a compound of formula XI-a:

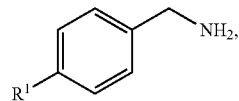

or a salt thereof, with 1,1'-carbonyldiimidazole (CDI). $R^1$ is a 2-methylpropan-oxy ("isobutoxy") group or a group that can be converted into an isobutoxy group. Suitable groups that can be converted into an isobutoxy group are apparent to those of skill in the art and include, for example, a hydroxyl group, a halogen, a mesylate or triflate group, or an alcohol protecting group. In certain embodiments, $R^1$ may be a halogen, a silyl ether or an alkoxy group. Preferably, $R^1$ is an isobutoxy group resulting in a compound of formula VI-a:

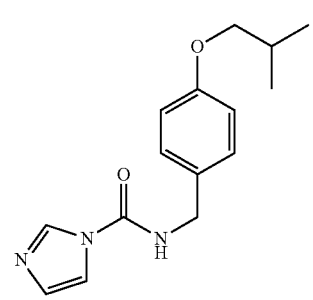

Thus, in one embodiment, the process comprises reacting a compound of formula XI, or a salt thereof, such as a hydrochloric acid addition salt, and 1,1'-carbonyldiimidazole ("CDI") to give the compound of formula VI-a, or a salt thereof, as illustrated by the following Scheme 3 (exemplified with $R^1$=isobutoxy).

Scheme 3:

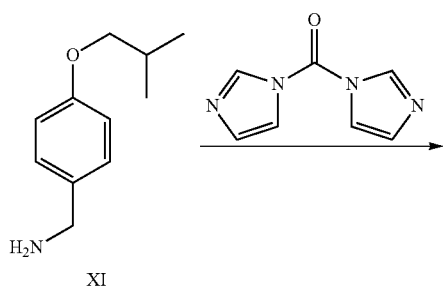

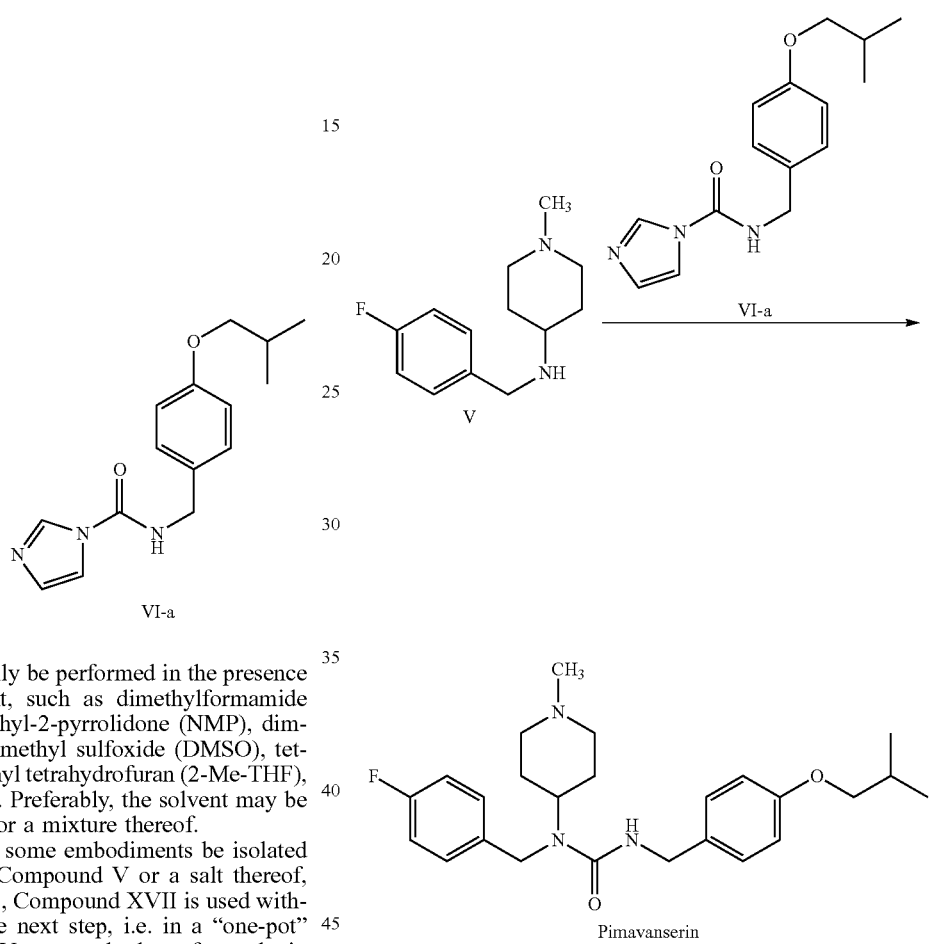

comprising reacting Compound XVII with Compound V, or a salt thereof, as illustrated by Scheme 4 (in Scheme 4 below, $R^1$ in formula XVII is isobutoxy, i.e. compound of formula VI-a, although the same reaction can of course also be carried out with other $R^1$ substituents that may later be converted to an isobutoxy group).

Scheme 4:

This process may generally be performed in the presence of suitable organic solvent, such as dimethylformamide (DMF), acetonitrile, N-methyl-2-pyrrolidone (NMP), dimethylformamide (DMA), dimethyl sulfoxide (DMSO), tetrahydrofuran (THF), 2-methyl tetrahydrofuran (2-Me-THF), toluene or mixtures thereof. Preferably, the solvent may be DMF, acetonitrile, toluene or a mixture thereof.

Compound XVII may in some embodiments be isolated prior to the reaction with Compound V or a salt thereof, while in other embodiments, Compound XVII is used without isolation directly in the next step, i.e. in a "one-pot" reaction, with Compound V, or a salt thereof, to obtain Pimavanserin or the corresponding precursor of Pimavanserin, wherein $R^1$ is a group that is converted into an isobutoxy group in a subsequent step.

Compounds of formula XVII, such as compound of formula VI-a, which are another aspect of the present disclosure, can be used as an intermediate in the synthesis of Pimavanserin, or salts thereof.

The intermediate compound of formula XVII may be converted to Pimavanserin or salts thereof by a process The reaction depicted in Scheme 4 can be carried out in a suitable organic solvent such as acetone at rather mild conditions (e.g. 40-50° C.). If necessary, the $R^1$ substituent may subsequently be converted to an isobutoxy group to obtain Pimavanserin or a salt thereof.

An overview about certain processes for preparation of Pimavanserin is shown in Scheme 5 below.

Scheme 5:

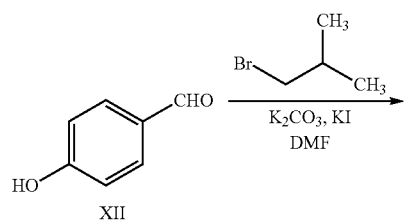

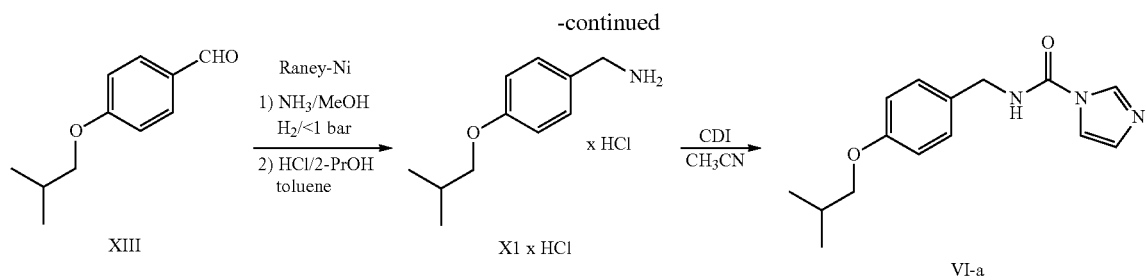

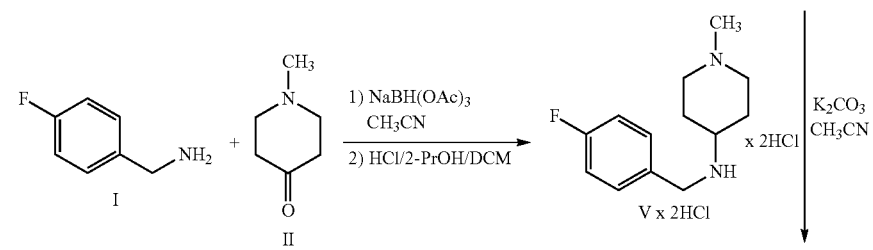

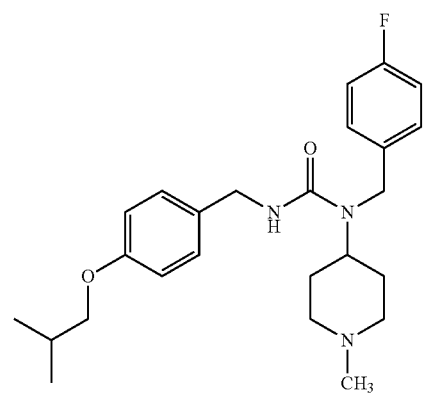

Compound A

L-Tartaric acid

Hemi-tartrate salt

*Compound A is Pimavanserin

Alternatively, the compound of formula XI-a, or a salt thereof, may also be reacted with 4-nitrophenyl chloroformate to yield a compound of formula Z:

Z

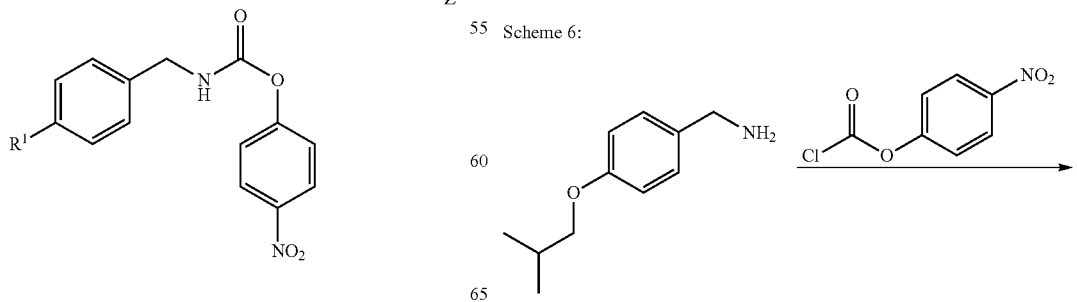

wherein $R^1$ is as defined above. This process step is illustrated in Scheme 6 (the Scheme depicts the reaction with compounds of formula XI and Y, respectively, i.e. with $R^1$=isobutoxy, although it can of course also be carried out with other groups that may later be converted into an isobutoxy group.

Scheme 6:

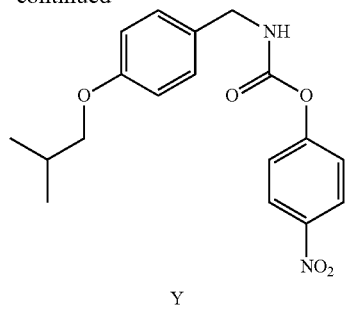

Y

This reaction may be carried out in a suitable organic solvent such as THF in the presence of a base, for example triethylamine, methylamine, N,N-diisopropylethylamine ("DIPEA"), 4-Dimethylaminopyridine (DMAP), potassium carbonate, sodium carbonate, cesium carbonate, or mixtures thereof. In some embodiments, the base is trimethylamine and/or the solvent is THF.

The compound of formula Z

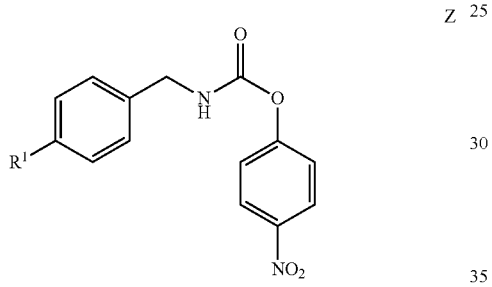

Z is a useful intermediate in the synthesis of Pimavanserin or salts thereof, and thus represents another aspect of the present disclosure.

As explained before, R¹ may in some embodiments be a 2-methylpropan-oxy ("isobutoxy") group, or a group that can be converted into an isobutoxy group. Preferably, R¹ is an isobutoxy group resulting in a compound of formula Y:

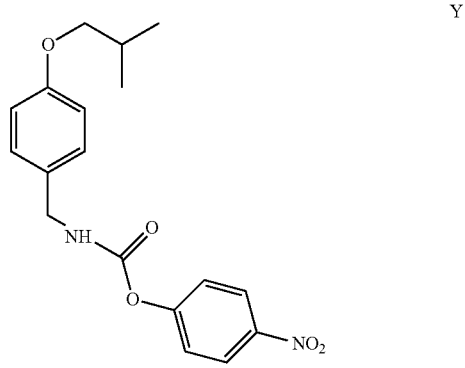 [SMILES: CC(C)COc1ccc(CNC(=O)Oc2ccc([N+](=O)[O-])cc2)cc1]

Y

The use of a compound of formula Z (or Y) in the preparation of Pimavanserin or a salt thereof, such as the hemi-tartrate salt of Pimavanserin represents therefore another aspect of the disclosure.

The conversion of compound of formula Z (or compound of formula Y) to Pimavanserin (or a precursor of Pimavanserin wherein R¹ is converted into an isobutoxy group in a subsequent step), or a salt thereof, may be accomplished by a process that comprises reacting Compound Z (or Y) with a compound V as illustrated by Scheme 7 below (shown with the specific example Compound Y).

Scheme 7:

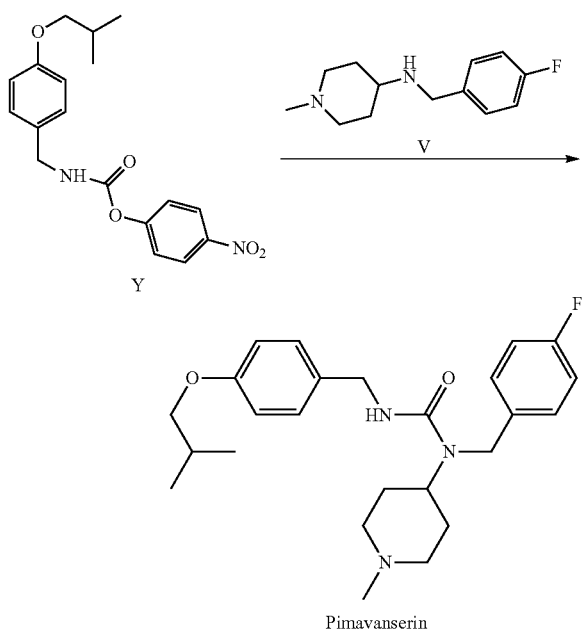

Pimavanserin

The reaction may be carried out in a suitable organic solvent, such as acetonitrile, and preferably includes a base, e.g. DMAP, as described for the analogous reaction of the compound of formula XVII with the compound of formula V.

If necessary, the residue R¹ may subsequently be converted to an isobutoxy group to obtain Pimavanserin, or a salt thereof. In one embodiment, the obtained Pimavanserin is further converted to the Pimavanserin hemi-tartrate salt.

In both process variants described herein above, the 4-substituted benzylamine of formula XI-a, or a salt thereof, may conveniently be prepared by converting a compound of formula XIII-a

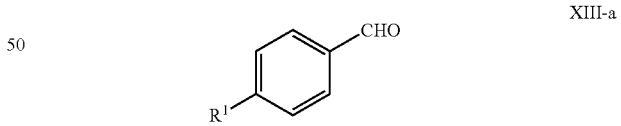

XIII-a to said compound of formula XI-a, or a salt thereof, by reductive amination via catalytic hydrogenation, e.g. with Raney Nickel, methanolic ammonia solution under hydrogen atmosphere, optionally followed by conversion into its acid addition salt (e.g. with HCl).

When R¹ is isobutoxy, the starting compound of formula XIII may in turn be obtained by reacting the 4-hydroxy-substituted precursor with isobutyl bromide in the presence of a base and catalytic amounts of potassium iodide (KI) in a suitable organic solvent such as DMF.

This process as depicted below in Scheme 8 (with R¹ being an isobutoxy group, yielding a compound of formula XI as a hydrochloric acid salt).

Scheme 8:

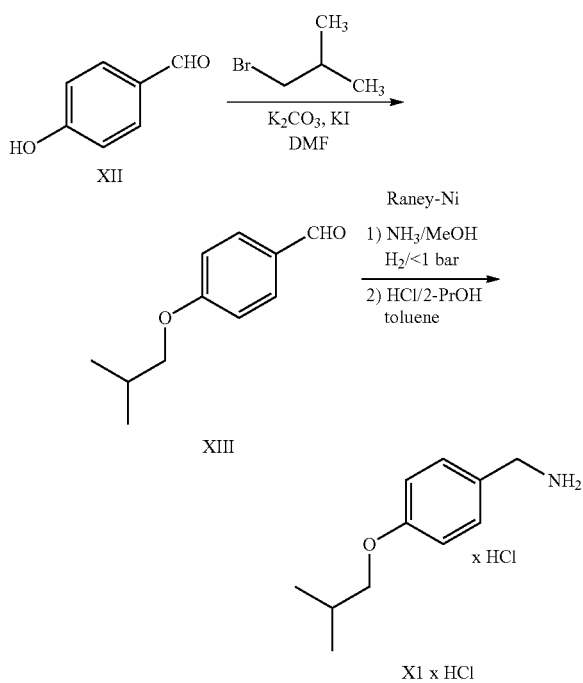

Alternatively, the compound of formula XI or XI-a may be prepared according to Scheme 9:

Scheme 9:

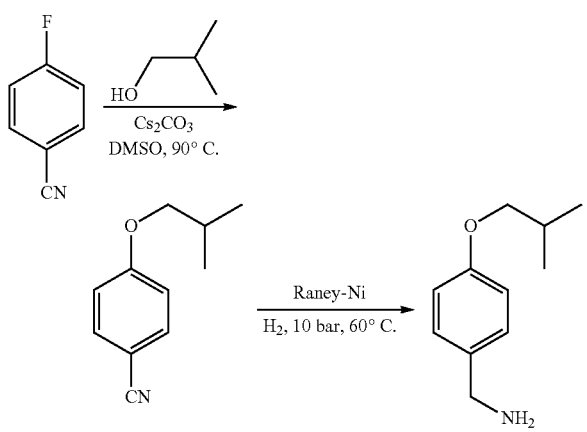

Figure 3:
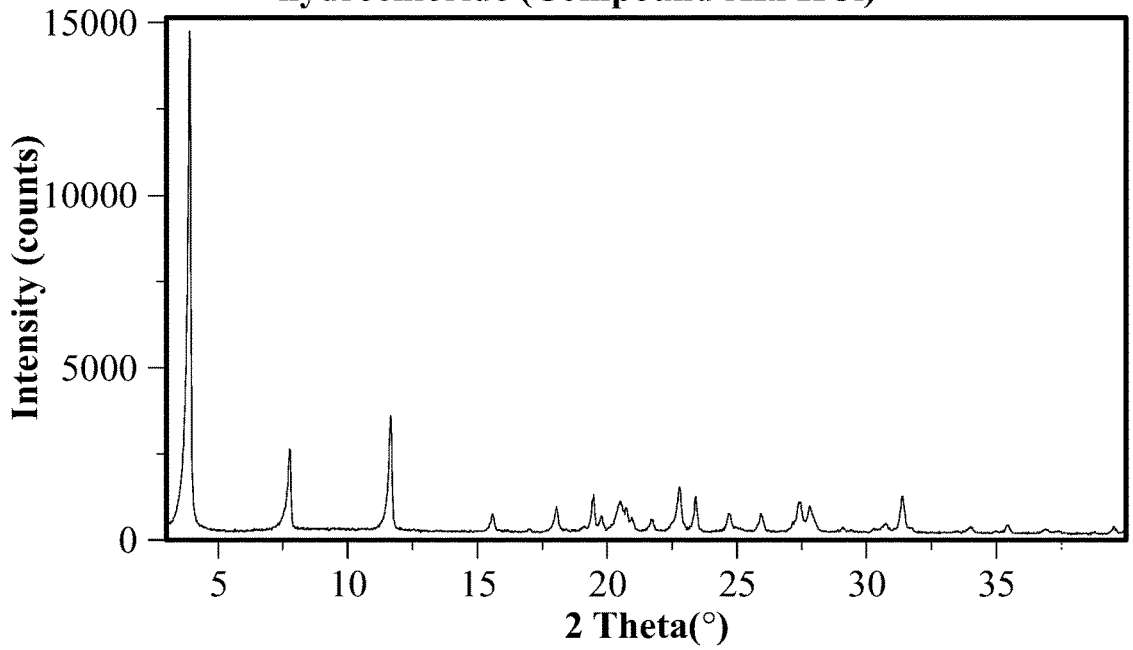
FIG. 3 shows a PXRD of crystalline form I of (4-isobutoxyphenyl)methanamine hydrochloride (Compound XI×HCl)
Figure 4:
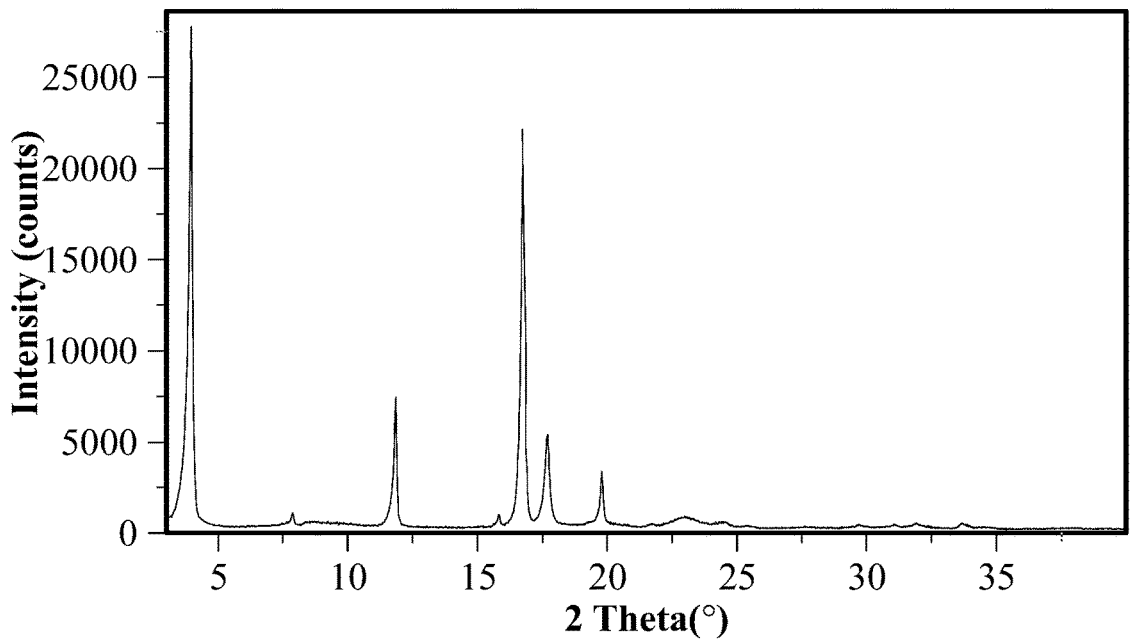
FIG. 4 shows a PXRD pattern of compound XVIII in a crystalline form I.
Figure 5:
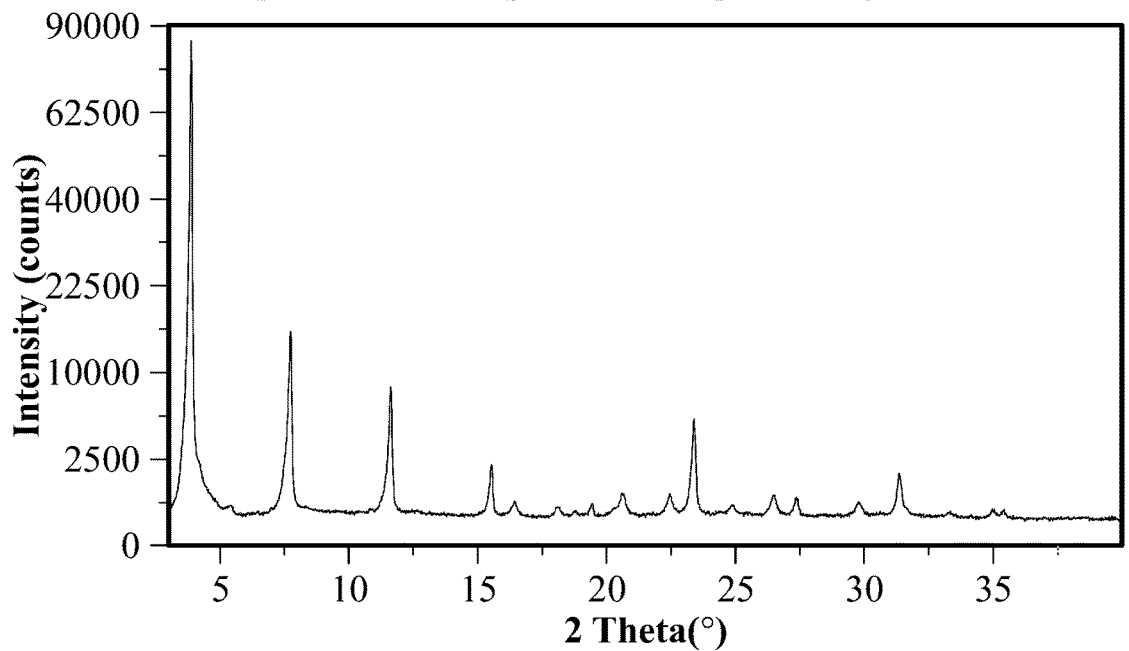
FIG. 5 shows a PXRD of compound XVIII in a crystalline form II.
Figure 6:
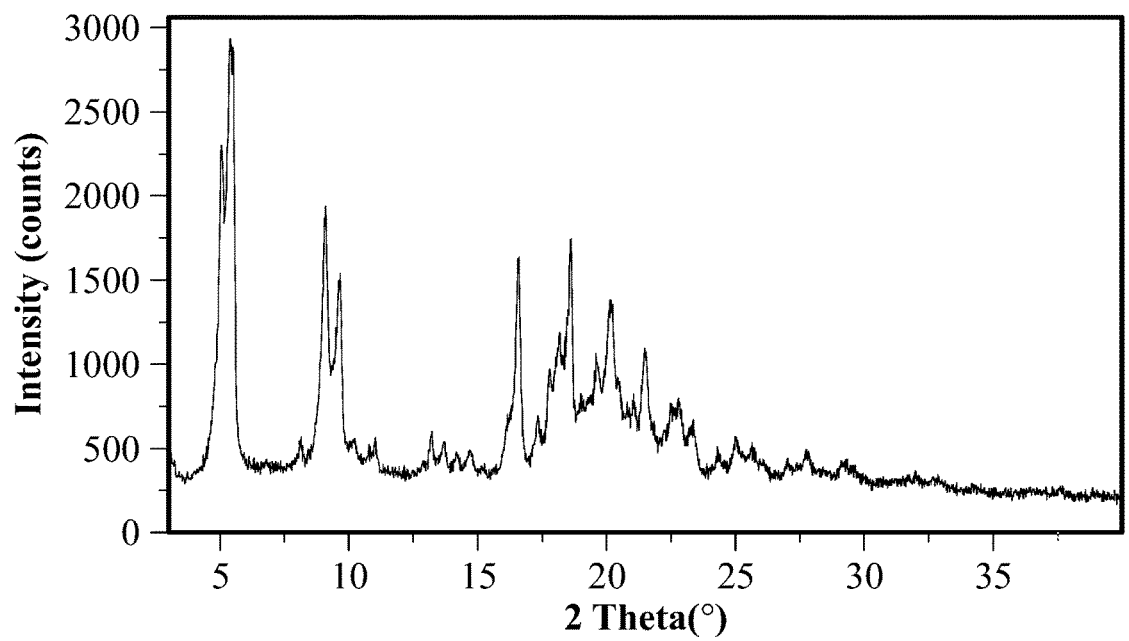
FIG. 6 shows a PXRD of crystalline Pimavanserin form X.

The present disclosure also includes the compound of formula XI as a hydrochloride salt in a crystalline form. The crystalline form, designated Form I, can be characterized by data selected from one or more of the following: X-ray powder diffraction pattern having peaks at about 3.9, 7.8, 11.7, 19.5 and 22.8 degrees two theta ±0.2 degrees two theta; an X-ray powder diffraction pattern as depicted in FIG. 3; and combinations of this data.

Crystalline Form I of Compound XI HCl can be further characterized by an X-ray powder diffraction pattern having peaks at 3.9, 7.8, 11.7, 19.5 and 22.8 degrees two theta ±0.2 degrees two theta and also having any one, any two, any three or more additional peaks selected from the group consisting of 15.6, 18.1, 20.5, 23.4 and 27.4 degrees two theta ±0.2 degrees two theta.

The disclosure further relates to a process which utilizes a hydroxamic acid derivative as an intermediate for producing Pimavanserin. Hydroxamic acid is known from U.S. Pat. No. 3,479,396; and reactions for the conversion of hydroxamic acid derivative to isocyanates are known from P. Dube et al. Org. Lett., Vol. 11, No. 24, 2009, 5622; or Zhao et al. Org. Process Res. Dev 2 Apr. 2015 (Web).

Thus, the present disclosure also relates to a novel N-hydroxy-2-(4-substituted)phenyl acetamide of the general formula XVIII:

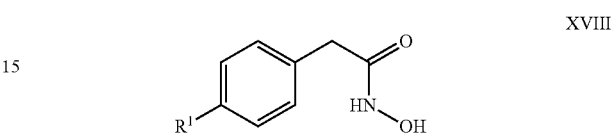

wherein $R^1$ is as defined above, i.e. a 2-methylpropan-oxy ("isobutoxy") group or a group that can be converted into an isobutoxy group. Preferably, $R^1$ is an isobutoxy group, and the resulting compound N-hydroxy-2-(4-isobutoxyphenyl)acetamide is referred to herein as "Compound 1".

In yet another aspect, the present disclosure provides a compound (referred to as Compound B) of the following formula:

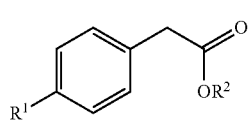

wherein $R^1$ is as defined above (preferably wherein $R^1$ is isobutoxy), and wherein $R^2$ may be alkyl, aryl or hydrogen. Preferably, $R^2$ is $C_1$-$C_6$ alkyl, such as methyl or ethyl, or phenyl, or hydrogen.

Compound B may be converted into a compound of formula XVIII. In some embodiments Compound B is reacted with hydroxylamine or hydroxylamine hydrochloride, in the presence of CDI, and a suitable solvent. In certain embodiments, $R^1$ is isobutoxy and $R^2$ is hydrogen.

Preferably, the solvent is an organic solvent such as acetonitrile, tetrahydrofuran (THF) or methyl-tetrahydrofuran (Me-THF), or mixtures thereof. Most preferably, the solvent is acetonitrile.

Alternatively, the compound of formula XVIII, such as Compound 1, can be prepared by hydroxylamination of methyl 2-(4-substituted phenyl)acetate. This reaction may be performed in the presence of hydroxylamine or hydroxylamine hydrochloride. In some embodiments, the hydroxylamination is performed in the presence of a base. Preferably the base is an inorganic base, such as sodium methoxide, potassium methoxide, potassium carbonate, sodium hydroxide or potassium hydroxide, or a mixture thereof and in the presence of a solvent. Preferably the solvent is an organic solvent, such as methanol, DMF, THF or Me-THF or a mixture thereof. Most preferably, the solvent is methanol.

The present inventors found that the compound of formula XVIII, such as Compound 1, is a useful intermediate for making Pimavanserin or a salt thereof. Hence, the use of Compound XVIII (or Compound 1) in the preparation of Pimavanserin, or a salt thereof represents another aspect of the present disclosure.

In the process of preparing Pimavanserin, Compound XVIII can be used either in an isolated form or prepared in situ, i.e. in a one-pot reaction. When used in isolated form, it may be in a crystalline form.

Accordingly, the present disclosure also includes Compound 1 (Compound XVIII with $R^1$ being isobutoxy-) in a crystalline form, designated form I, characterized by data selected from one or more of the following: an X-ray powder diffraction pattern having peaks at about 4.0, 11.9, 16.8, 17.7 and 19.8° 2θ±0.2° 2θ; an X-ray powder diffraction pattern as depicted in FIG. 1; and combinations of this data.

Crystalline form I of Compound 1 may be further characterized by an X-ray powder diffraction pattern having peaks at 4.0, 11.9, 16.8, 17.7 and 19.8° 2θ±0.2° 2θ and also having any one, any two, any three additional peaks selected from 7.9, 15.8 and 23.0° 2θ±0.2° 2θ.

Crystalline form I of Compound 1 may be characterized by each of the above characteristics alone and/or by all possible combinations.

Figure 2:
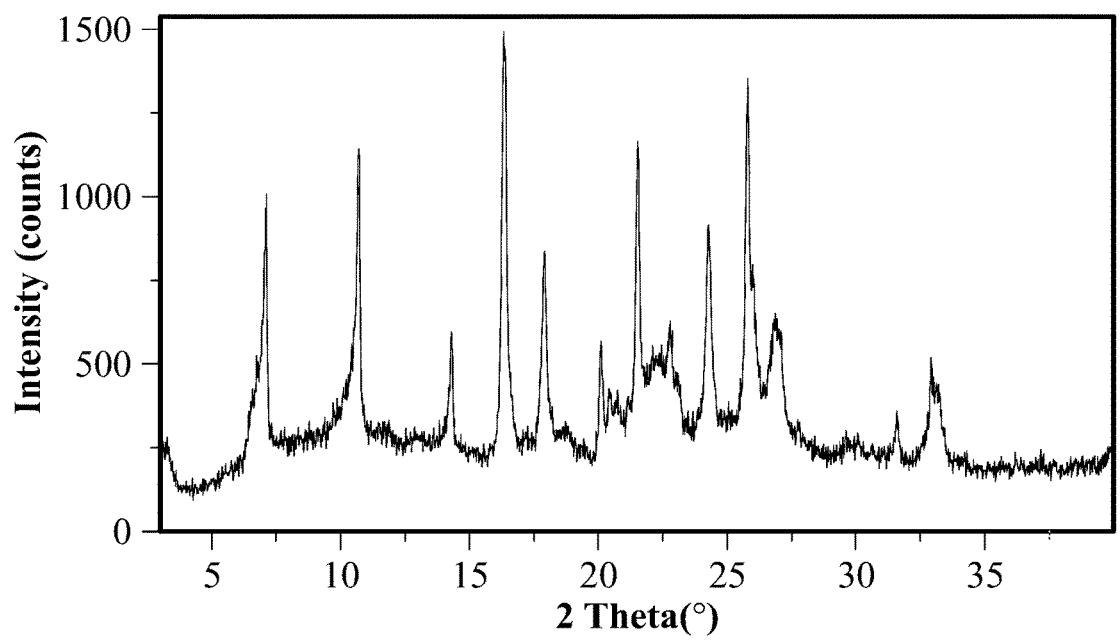
FIG. 2 shows a PXRD of crystalline form II of N-(4-fluorobenzyl)-1-methylpiperidin-4-amine dihydrochloride (Compound V×2 HCl)

Compound 1 in another crystalline form, designated form II, is another embodiment and can be characterized by data selected from one or more of the following: an X-ray powder diffraction pattern having peaks at about 3.9, 7.8, 11.6, 15.5 and 23.4° 2θ±0.2° 2θ; an X-ray powder diffraction pattern as depicted in FIG. 2; and combinations of this data.

Crystalline form II of Compound 1 can be further characterized by an X-ray powder diffraction pattern having peaks at 3.9, 7.8, 11.6, 15.5 and 23.4° 2θ±0.2° 2θ and also having any one, any two, any three or more additional peaks selected from 16.4, 20.7, 22.5, 26.5 and 31.7° 2θ±0.2° 2θ.

Crystalline form II of Compound 1 may be characterized by each of the above characteristics alone and/or by all possible combinations.

The compound of formula XVIII (such as Compound 1) can be converted to Pimavanserin, or a salt thereof, by reacting it with CDI to obtain an intermediate of formula XIX (as shown below) which is then converted to Pimavanserin (or the respective derivative where $R^1$ is only converted to isobutoxy in a subsequent step), or a salt thereof.

This process can be illustrated by the following Scheme 10 (Compound 1 is shown as an illustrative example):

Scheme 10:

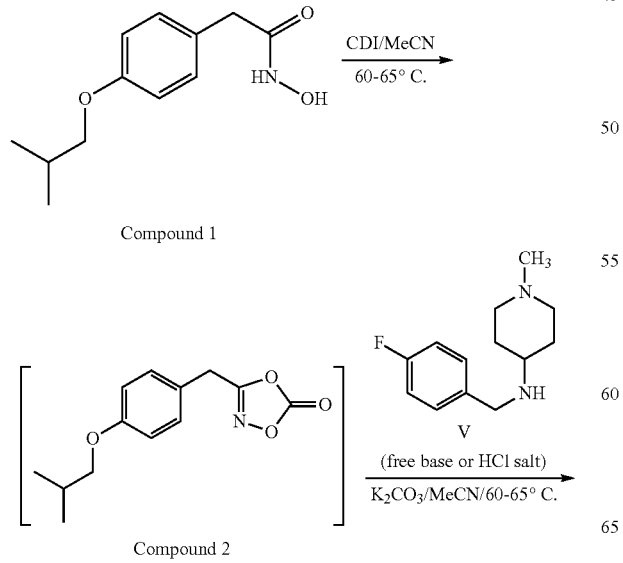

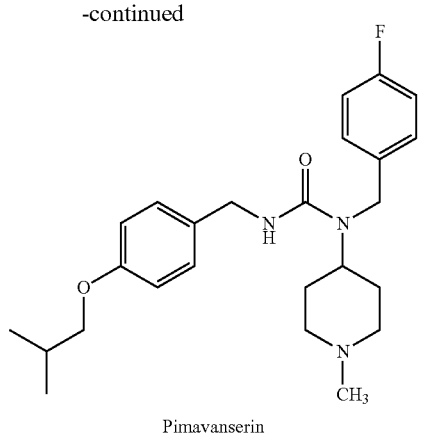

Pimavanserin

Thus, in certain embodiments, the process comprises
a) reacting a compound of formula XVIII, such as Compound 1, with 1,1'-carbonyldiimidazole (CDI) to obtain 3-(4-substituted benzyl)-1,4,2-dioxazol-5-one (referred to herein as a compound of formula XIX); and
b) reacting the obtained compound of formula XIX with Compound V or a salt thereof (e.g. the dihydrochloride salt) to obtain Pimavanserin, or a salt thereof.

In certain embodiments, step a) is performed in the presence of a solvent. Suitable solvents include for example acetonitrile, tetrahydrofuran (THF) or methyl-tetrahydrofuran (Me-THF), or mixtures thereof. Preferably, the solvent is acetonitrile.

The above reaction may be performed at a temperature of from about 20° C. to about 80° C. Preferably, the temperature is about 50° C. to about 70° C. More preferably, the temperature is about 60° C. to about 65° C.

As can be seen from Scheme 10 above, the reaction of the compound of formula XVIII with CDI proceeds via the intermediate of formula XIX (5-([4-substituted]benzyl)-1,3,4-dioxazol-2-one):

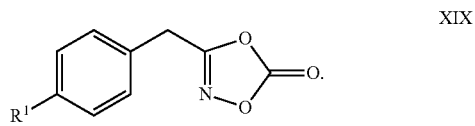

The intermediate of formula XIX as well as the process for preparing it by reacting the compound of formula XVIII with CDI thus represent further aspect of the disclosure.

As detailed above, $R^1$ may be a 2-methylpropan-oxy ("isobutoxy") group or a group that can be converted into an isobutoxy group. In embodiments where $R^1$ is an isobutoxy group, the compound of formula XIX is referred to herein as Compound 2 (5-((4-isobutoxy)-benzyl)-1,3,4-dioxazol-2-one):

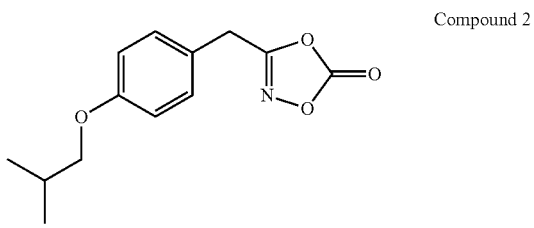 [SMILES: CC(C)COc1ccc(Cc2noc(=O)o2)cc1]

The intermediate of formula XIX (such as Compound 2) can be used in the preparation of Pimavanserin, or a salt thereof, which therefore represents yet another aspect of the present disclosure.

In the process going through the intermediate of formula XIX/Compound 2 (typically starting form a compound of formula XVIII such as the specific Compound 1), the intermediate may be isolated before reacting it with the compound of formula V.

Alternatively, the reaction is performed without the isolation of the intermediate of formula XIX/Compound 2, i.e. as a one-pot reaction.

Compound V can be prepared according to US '740, or, alternatively, by reacting 4-fluorobenzaldehyde (referred to herein as compound of formula III) and 1-methylpiperidin-4-amine (referred to herein as compound of formula IV) in the presence of a reducing agent, as illustrated by Scheme 11:

Scheme 11:

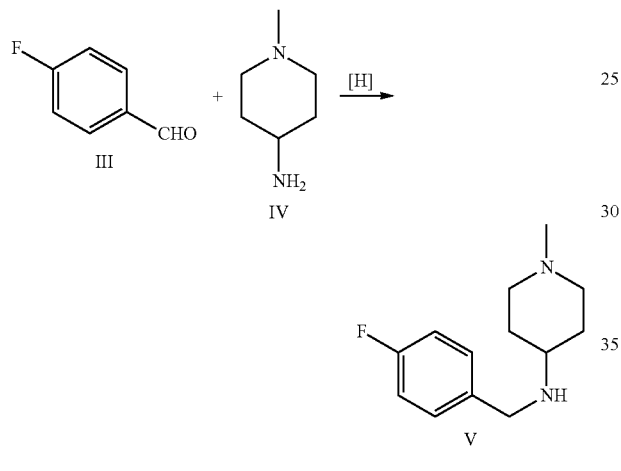

This process represents another aspect of the present disclosure. In certain embodiments, the processes for preparing Pimavanserin, or a salt thereof include the step of preparing compound of formula V via the compounds of formula III and IV.

The isobutoxy substituent in position $R^1$ present in many compounds disclosed herein can for example be created by reacting (an optionally protected/derivatized) phenolic hydroxyl group with an alkylation agent, for example, 1-bromo-2-methylpropane, 1-iodo-2-methylpropane, or 1-chloro-2-methylpropane. Preferably, the alkylation agent for this reaction step is 1-bromo-2-methylpropane. The alkylation may be performed in the presence of a base. Preferably, the base is an inorganic base. More preferably, the base is potassium carbonate, sodium carbonate, or cesium carbonate, or a mixture thereof. Most preferably, the base is potassium carbonate. In other embodiments, this reaction may be performed in the presence of a solvent. Preferably, the solvent is a polar solvent. More preferably, the solvent is dimethylformamide (DMF), N-methyl-2-pyrrolidone (NMP), dimethylacetamide (DMA) or dimethyl sulfoxide (DMSO). Most preferably, the solvent is DMF.

In the processes for preparing Pimavanserin as described herein, Pimavanserin may be obtained in a crystalline form.

In a specific embodiment, the present disclosure includes crystalline Pimavanserin designated form X, characterized by data selected from one or more of the following: X-ray powder diffraction pattern having peaks at about 5.1, 5.4, 9.1, 9.7 and 16.6° 2θ±0.2° 2θ; an X-ray powder diffraction pattern as depicted in FIG. 3; and combinations of this data.

Crystalline Pimavanserin form X may be further characterized by the X-ray powder diffraction pattern having peaks at 5.1, 5.4, 9.1, 9.7 and 16.6° 2θ±0.2° 2θ and also having any one, any two, any three additional peaks selected from 17.8, 18.2, 18.6, 20.2 and 21.5° 2θ±0.2° 2θ.

Crystalline Pimavanserin form X may be characterized by each of the above characteristics alone and/or by all possible combinations. Form X may for example be obtained according to the procedure outlined in Example 35.

In some embodiments, the obtained Pimavanserin may be further converted to a salt, preferably, a pharmaceutically acceptable salt. For example, Pimavanserin may be converted to its hemi-tartrate salt. The conversion can be done either directly, i.e. in a one-pot manner, or with isolation of Pimavanserin prior to the conversion into the respective salt.

The present disclosure also describes the use of tetraalkylammonium isocyanate in the preparation of Pimavanserin and salts thereof.

These processes comprise reacting said tetraalkylammonium isocyanate with (4-isobutoxyphenyl)methanol in the presence of 2,4,6-trichloro[1,3,5]triazine to obtain 1-isobutoxy-4-(isocyanatomethyl)benzene (referred to as Compound XVI). This step can be illustrated by Scheme 12.

Scheme 12:

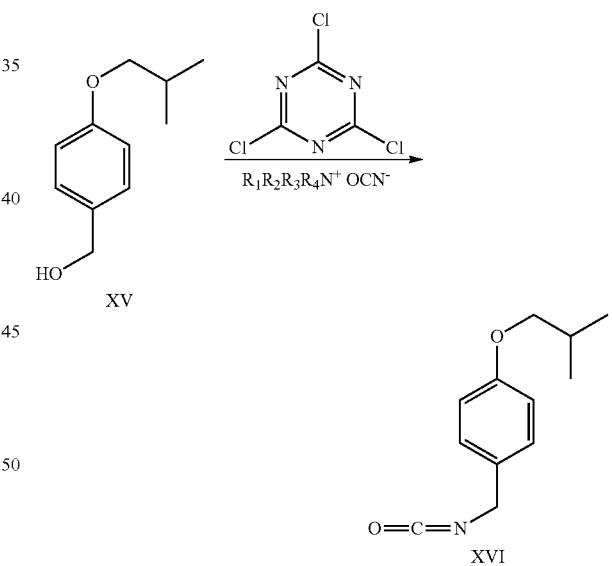

In this scheme, $R_1$, $R_2$, $R_3$ and $R_4$ can be the same or different, and, independently, may be an alkyl, aryl or alkyl-aryl. In certain embodiments, $R_1$, $R_2$, $R_3$, and $R_4$ are, independently, alkyl. In other embodiments, $R_1$, $R_2$, $R_3$, and $R_4$ are, independently, $C_1$-$C_6$ alkyl. In further embodiments, $R_1$, $R_2$, $R_3$, and $R_4$ are, independently, $C_4$ alkyl. In still further embodiments, $R_1$, $R_2$, $R_3$, and $R_4$ are, independently, n-butyl.

Compound XVI can then be converted to Pimavanserin by reacting it with N-(4-fluorobenzyl)-1-methylpiperidin-4-amine (compound of formula V), as shown in Scheme 13.

Scheme 13:
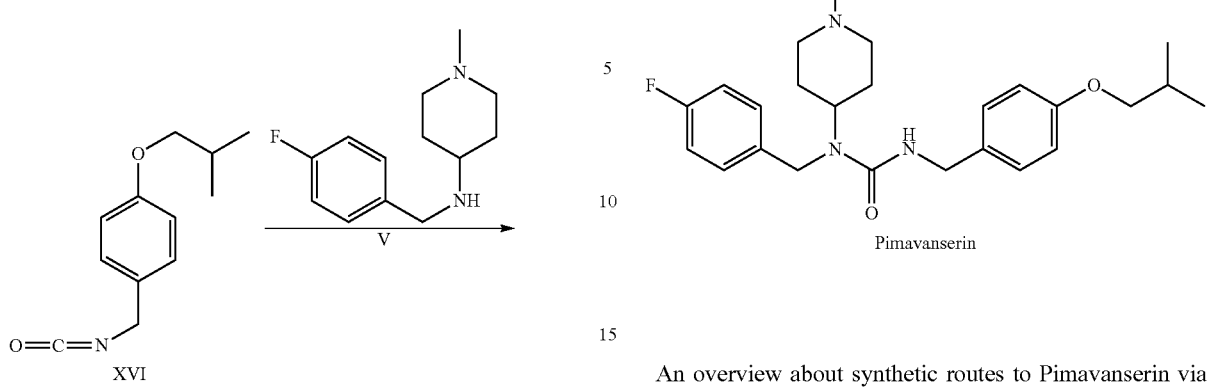
Pimavanserin
An overview about synthetic routes to Pimavanserin via Compound XVI is shown in the following Scheme 14:
Scheme 14:
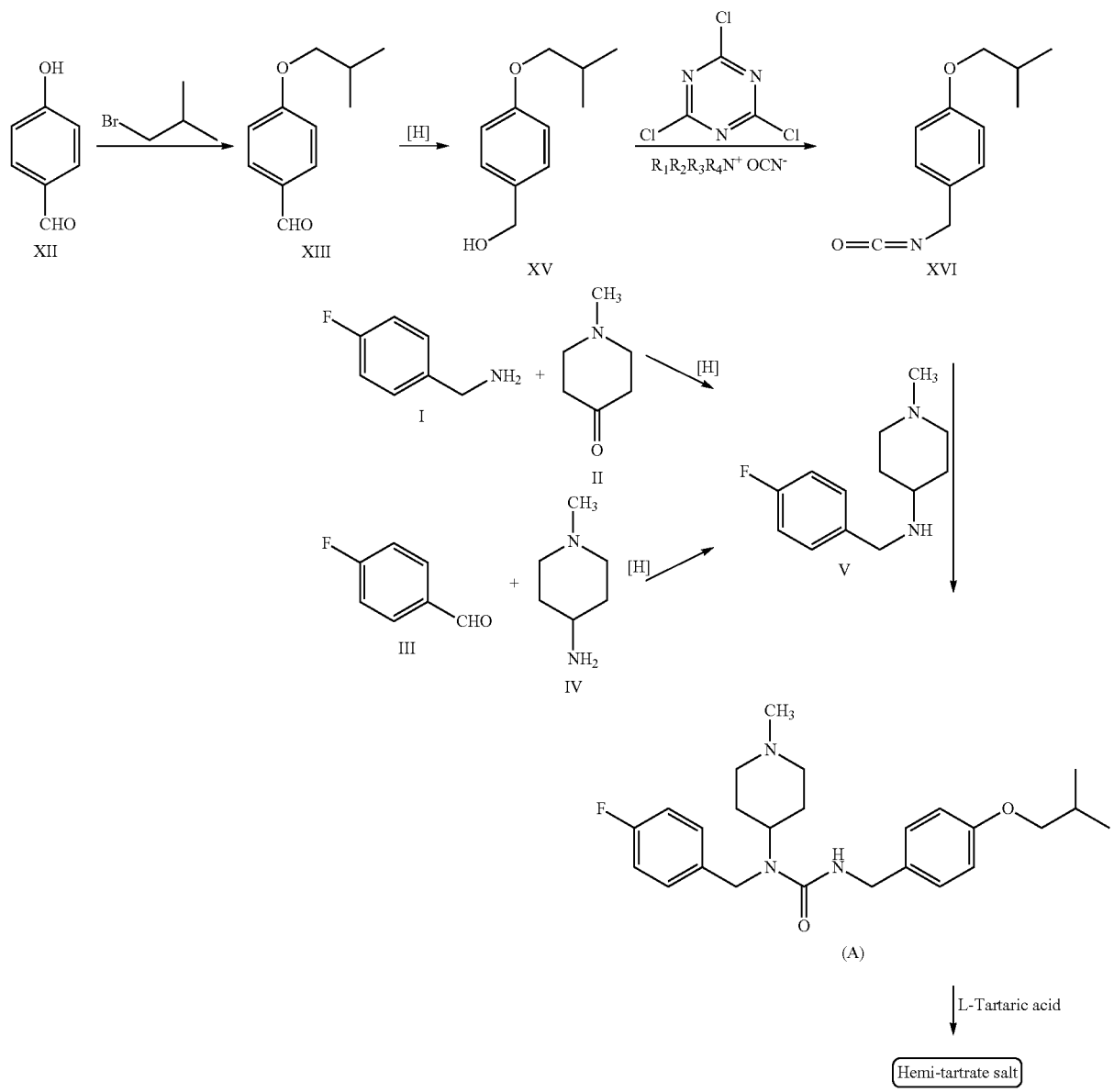

In this scheme, $R_1$, $R_2$, $R_3$ and $R_4$ are as defined above, with compound (A) being Pimavanserin.

Further described herein is a compound of formula VI:

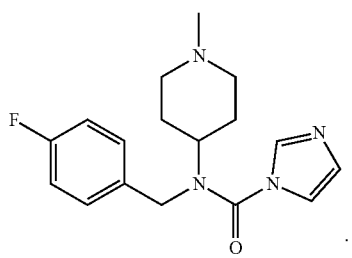

VI

The compound of formula VI may be employed as a useful intermediate in the synthesis of Pimavanserin or a salt thereof. Such a process involves reacting the compound of formula VI with a compound of formula XI-a XI-a wherein $R^1$ is a 2-methylpropan-oxy ("isobutoxy") group or a group that can be converted into an isobutoxy group, to obtain Pimavanserin or a salt thereof. Preferably, $R^1$ is isobutoxy (referred herein as a compound of formula XI).

Moreover, the compound of formula XI-a (such as XI) may be first converted to a salt, such as a hydrochloric acid addition salt, before reacting it with Compound VI.

This process is illustrated in Scheme 15:

Scheme 15:

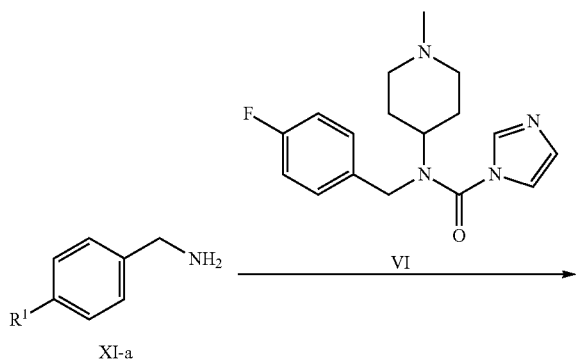

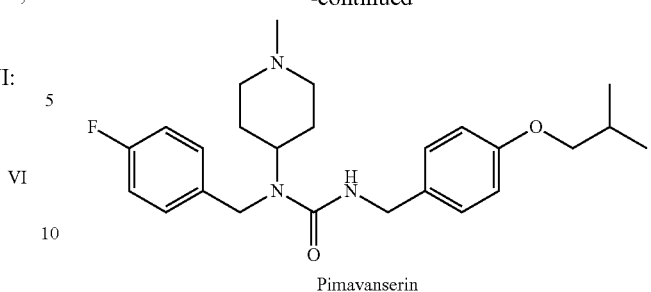

Pimavanserin

The compound of formula VI itself may be prepared by a process comprising reacting N-(4-fluorobenzyl)-1-methyl-piperidin-4-amine (Compound of formula V) and 1,1'-carbonyldiimidazole ("CDI"), as illustrated by Scheme 16 below.

Scheme 16:

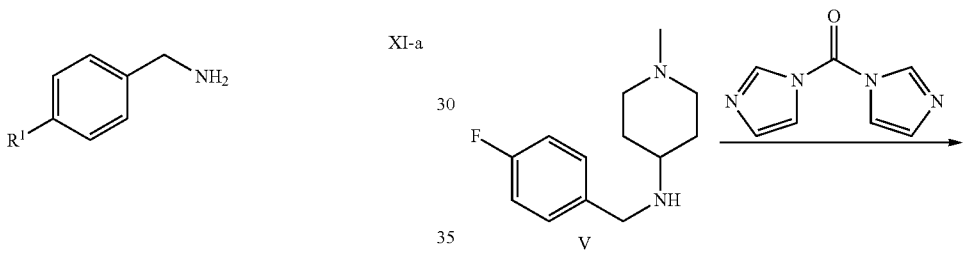

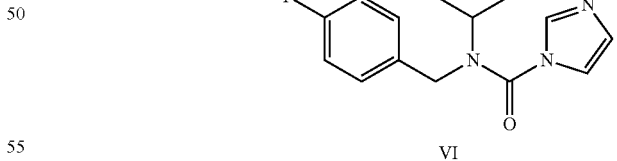

VI

The reaction illustrated by Scheme 16 may be carried out in a polar solvent such as acetone, optionally in the presence of some additional imidazole and/or imidazole hydrochloride.

An overview about certain processes for the preparation of Pimavanserin as described herein is shown in Scheme 17 below.

Scheme 17:

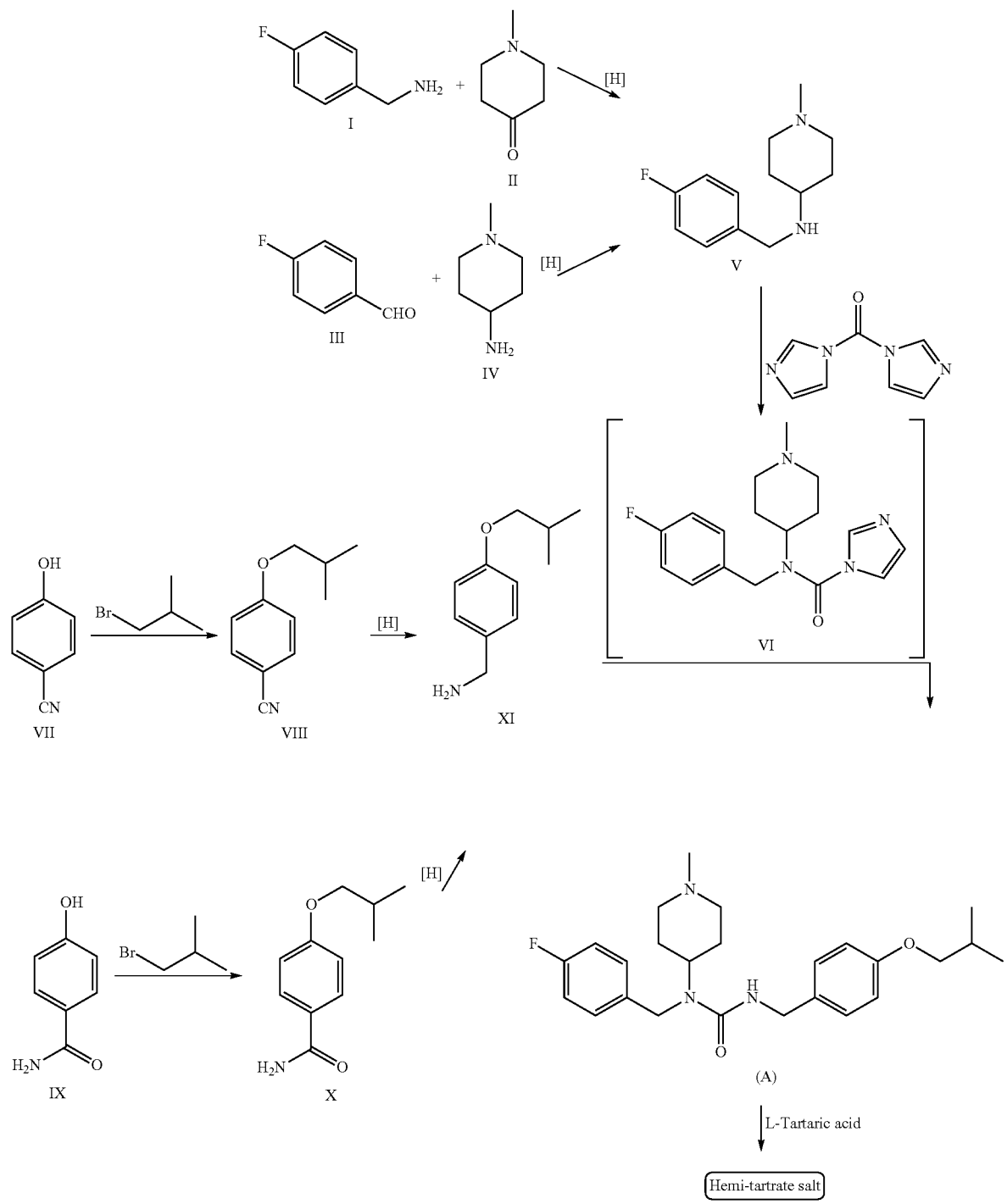

Powder X-Ray Diffraction ("XRPD" or "PXRD") Method

The sample, after being carefully powdered in a mortar and pestle, is applied directly on a silicon plate holder. The X-ray powder diffraction pattern was measured with a Philips X'Pert PRO X-ray powder diffractometer, equipped with Cu K$_\alpha$ irradiation source (wavelength 1.54184 Å) and X'Celerator (2.022° 2θ) detector. Scanning parameters: angle range: 3-40°, step size 0.0167, time per step 37 s, continuous scan.

Having described the disclosure with reference to certain preferred embodiments, other embodiments will become apparent to one skilled in the art from consideration of the specification. The disclosure is further defined by reference to the following examples describing in detail the preparation of the composition and methods of use of the disclosure. It will be apparent to those skilled in the art that many modifications, both to materials and methods, may be practiced without departing from the scope of the disclosure.

EXAMPLES

Example 1: Preparation of N-(4-fluorobenzyl)-1-methylpiperidin-4-amine Preparation (Option 1)

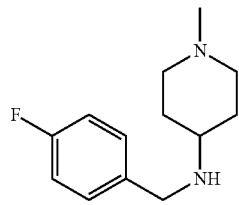

V

Methanol is added to an Erlenmeyer flask and acetic acid is added under stirring until pH 5. 4-Fluorobenzylamine and 1-methylpiperidin-4-one are added to a round-bottomed flask and dissolved in the methanol/acetic acid solution previously made. The reaction mixture is stirred for 5 min and $NaCNBH_3$ is added slowly under stirring. After 20 hours, the reaction is concentrated and transferred to a separatory funnel containing dichloromethane and distilled water. The aqueous phase was made basic by addition of $Na_2CO_3$. The aqueous phase is extracted twice with dichloromethane. The combined organic layers are collected and dried with $Na_2SO_4$. Concentration afforded N-(4-fluorobenzyl)-1-methylpiperidin-4-amine.

Example 2: Preparation of N-(4-fluorobenzyl)-1-methylpiperidin-4-amine Preparation (Option 2)

Reacting 4-fluorobenzaldehyde (1.25 g; 10 mmol; 1.0 eq) and 1-methylpiperidin-4-amine (1.13 g; 10 mmol; 1.0 eq) in the presence of $NaCNBH_3$ (0.83 g; 12.2 mmol) in methanol/acetic acid mixture (40 ml) at pH 5 during about 20 hours under ambient conditions leads to N-(4-fluorobenzyl)-1-methylpiperidin-4-amine formation. The reaction mixture is concentrated and transferred to a separatory funnel containing dichloromethane and distilled water. The aqueous phase is made basic by addition of $Na_2CO_3$. The aqueous phase is extracted twice with dichloromethane. The combined organic layers are collected and dried with $Na_2SO_4$. Concentration afforded N-(4-fluorobenzyl)-1-methylpiperidin-4-amine.

Example 3: Preparation of N-(4-isobutoxybenzyl)-1H-imidazole-1-carboxamide

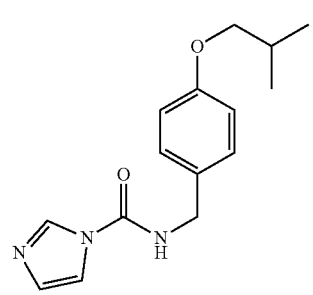

VI-a

Reacting (4-isobutoxyphenyl)methanamine (9.14 g, 51 mmol; 1.0 eq) with 1,1'-Carbonyldiimidazole (CDI) (9.95 g; 61 mmol; 1.2 eq) in the presence of imidazole (0.175 g; 2 mmol; 0.05 eq) and imidazole hydrochloride (0.995 g; 9 mmol; 0.186 eq) in acetone (30 ml) at 10° C. during about 2 hours leads to formation of N-(4-isobutoxybenzyl)-1H-imidazole-1-carboxamide intermediate.

Example 4: Preparation of 1-(4-fluorobenzyl)-3-(4-isobutoxybenzyl)-1-(1-methylpiperidin-4-yl)urea (Compound A)

Reacting N-(4-isobutoxybenzyl)-1H-imidazole-1-carboxamide intermediate (reaction mixture in acetone) obtained in Example 5 with N-(4-fluorobenzyl)-1-methylpiperidin-4-amine (9.56 g, 43 mmol; 0.85 eq), obtained in Examples 1 or 2, in acetone (60 ml) at 40-50° C. during about 3 hours leads to 1-(4-fluorobenzyl)-3-(4-isobutoxybenzyl)-1-(1-methylpiperidin-4-yl)urea (Compound A) formation. The target product is precipitated and isolated by addition of water (100 ml), stirring under ambient temperature for about 20 hours, filtration and drying.

Example 5: Preparation of 4-isobutoxybenzonitrile

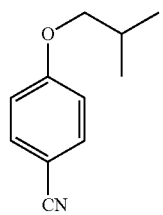

4-Hydroxybenzonitrile (59.6 g, 0.5 mol), potassium carbonate (276.4 g, 2.0 mol), potassium iodide (33.2 g, 0.2 mol) are mixed with dimethylformamide (1 L). 1-Bromo-2-methyl propane (217.5 ml, 2.0 mol) is added to the resulting suspension at 70° C. The alkylation reaction is performed at 70° C. for 6 hours. The resulting reaction mixture is filtered in order to remove inorganic salts from the reaction mixture. The filtrate is concentrated to about 300 ml. The residue is mixed with water and methyl tert-butyl ether. The organic phase is separated, washed with saturated brine and dried over magnesium sulfate. After concentrating the solution is purified by silica gel column chromatography (5-7% ethyl acetate/hexanes) to give 4-iso-butoxybenzonitrile (84.6 g, 96.5%).

Example 6: Preparation of (4-isobutoxyphenyl)methanamine (Option 1)

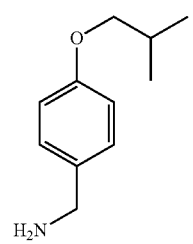

A solution of 4-isobutoxybenzonitrile (6.2 mmol) in ammonia in methanol (2 N) (30 ml) is charged with Raney Nickel (25 mg) and is stirred under hydrogen at 60° C. for 4 hrs, upon which LCMS indicated the disappearance of starting material. The reaction mixture is filtered through a pad of celite and the filtrate is concentrated in vacuo to afford (4-isobutoxyphenyl)methanamine.

Example 7: Preparation of 4-isobutoxybenzamide

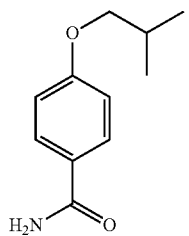

Reacting 4-hydroxybenzonitrile with 1-bromo-2-methyl propane in the presence of potassium carbonate in DMF/toluene mixture for 3 hrs at about 80° C. leads to 4-iso-butoxybenzamide formation. 4-Iso-butoxybenzamide is isolated from the reaction mixture by hot filtration in order to remove inorganic salts. The filtrate is concentrated and mixed with water and methyl tert-butyl ether. The organic phase is separated, washed with saturated brine, dried over magnesium sulfate and evaporated to dryness to afford the target product.

Example 8: Preparation of (4-isobutoxyphenyl)methanamine (Option 2)

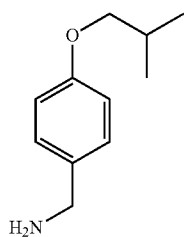

Sodium borohydride, diglyme (90 ml), 4-iso-butoxybenzamide and octadecane (1.5 ml) are reacted at 162° C. for about 1.5 hrs (GC monitoring). The reaction mixture is quenched with aqueous ammonium chloride (pH=8.5) and extracted into methylene chloride. (4-Isobutoxyphenyl)methanamine is isolated by removing solvent and distillation.

Example 9: Preparation of (4-Isobutoxyphenyl)methanol

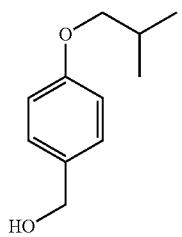

A solution of 4-isobutoxybenzaldehyde (6.24 g, 35 mmol) in THF (80 ml) is added dropwise to a stirred suspension of NaBH$_4$ (2.65 g, 70 mmol) in dry THF (70 ml) at 0° C. The reaction mixture is stirred at room temperature overnight and is quenched with a small amount of water (5 ml). The solid formed is removed by filtration and the filtrate is concentrated in vacuo. The residue is dissolved in CHCl$_3$ (50 ml). The resulting solution is washed with brine (3×20 mL), dried over anhydrous Na$_2$SO$_4$, and concentrated in vacuo to give (4-isobutoxyphenyl)methanol.

Example 10: Preparation of 4-isobutoxybenzonitrile

To a 500 mL, three necks, round bottom flask, equipped with the stir bar, thermocouple and nitrogen sweep, was charged 24.59 g of 4-fluorobenzonitrile (1) (FW: 121.1, 203.1 mmol, 1.0 equiv.), 86.0 g of cesium carbonate (FW: 325.82, 264.0 mmol, 1.3 equiv.), 37.5 mL of isobutanol (FW: 74.12, 406.2 mmol, 2.0 equiv.), followed by 150 mL (6 vol.) of DMSO. The resultant mixture was heated to 90° C., and stirred at this temperature for 4.5 hours. HPLC analysis indicated 31 A % of starting material remaining. Additional 14.0 g of cesium carbonate (FW: 325.82, 43.0 mmol, 0.2 equiv.) was charged, and the reaction was kept stirring at 90° C. for approximately 24 hours until reaction completion. The batch was cooled down to room temperature and diluted with 500 mL of DI water (20 vol.), extracted with 250 mL (10 vol.) of ethyl acetate. After partition, the product was in the upper organic layer, which was washed with 4×250 mL of DI water before concentrating to dryness under vacuum to afford 34.45 g of 4-isobutoxybenzonitrile as a light yellow liquid, representing a 96.9% yield in 98.7 A % purity. 1H NMR (CDCl$_3$, 400 MHz): δ=1.03 (d, J=6.8 Hz, 6H), 2.06-2.14 (m, 1H), 3.76 (d, J=6.4 Hz, 2H), 6.94 (dd, J=2.0, 7.6 Hz, 2H), 7.56-7.59 (m, 2H). GC/MS CH4/CI (m/z): [M+1]+=176.09.

Example 11: Preparation of Compound XI

To a 500 mL Buch autoclave, equipped with an overhead stirrer, thermocouple and nitrogen sweep, was charged 25 g of Raney Nickel (100 wt %), and a solution of 25 g of 4-isobutoxybenzonitrile (FW: 175.23, 143 mmol, 1.0 equiv.) in 250 mL of MeOH (10 vol.) through a funnel. After addition, the funnel was rinsed with 25 mL (1 vol.) of MeOH, the wash was combined into the batch. The autoclave was properly sealed, and exchanged to 10 bar of hydrogen atmosphere. The batch was heated to 55° C. and stirred at the same temperature for approximately 1 hour until no hydrogen was taken in. Additional 7.8 g of Raney Nickel was charged, but the reaction stalled without further progressing. The batch was filtered on Buchner funnel with a celite pad (filter cake has to be kept wet). The filter cake was washed with 2×50 mL (2 vol.) of MeOH. The combined filtrate was concentrated to dryness. The residue was purified by silica gel chromatography, eluting with 10% MeOH in methylene chloride in the presence of 2% of ammonium hydroxide to afford 7.63 g of Compound XI as a hemi-solidified liquid, representing a 35% yield in 99.7 A % purity. 1H NMR (DMSO-$d_6$, 400 MHz): δ=0.97 (d, J=6.4 Hz, 6H), 1.94-2.04 (m, 1H), 3.62 (s, 2H), 3.70 (d, J=6.4 Hz, 2H), 6.84 (d, J=8.8 Hz, 2H), 7.21 (d, J=8.8 Hz, 2H). HRMS-ESI (m/z): [M+Na]+ Calcd for $C_{25}H_{35}F_1N_3O_2$: 202.1202; found 202.1207.

Example 12: Preparation of Compound XI

To a 250 mL, three necks, round bottom flask, equipped with the stir bar, thermocouple and nitrogen sweep, was charged 5.0 g of 4-isobutoxybenzonitrile (FW: 175.23, 28.5 mmol, 1.0 equiv.), 9.37 g of cesium carbonate (FW: 325.82, 28.5 mmol, 1.0 equiv.), followed by 50 mL (10 vol.) of DMSO and 5 mL (1 vol.) of DI water. After heating to 95° C., 4.9 mL of 30% hydrogen peroxide aqueous solution (FW: 34, 48.5 mmol, 1.7 equiv.) was charged in 20 minutes. HPLC analysis indicated the reaction completed instantly after charging. The batch was cooled down to room temperature and diluted with 100 mL of DI water (20 vol.). The product precipitated, and collected by vacuum filtration. The filter cake was washed with 50 mL of DI water (10 vol), and dried in the Buchner funnel with nitrogen sweep for 1 hour before transferring into vacuum oven, drying at 80° C. under full house vacuum for 20 hours. This afforded 5.147 g of 4-isobutoxybenzamide as a white solid, representing a 93.6% yield in 99.8 A % purity. 1H NMR (CDCl$_3$, 400 MHz): δ=1.04 (d, J=7.6 Hz, 6H), 2.05-2.15 (m, 1H), 3.77 (d, J=6.4 Hz, 2H), 5.59 (brs, 1H), 5.95 (brs, 1H), 6.93 (d, J=8.8 Hz, 2H), 7.77 (d, J=8.8 Hz, 2H). GC/MS CH$_4$/CI (m/z): [M+1]+=194.16.

Example 13: Preparation of Compound XI

To a 250 mL, three necks, round bottom flask, equipped with a stir bar, condenser, thermocouple and nitrogen sweep, was charged 2.34 g of 4-isobutoxybenzamide (FW: 193, 12.1 mmol, 1.0 equiv.), followed by 47 mL (20 vol.) of THF. After cooling to 0-5° C., 4.1 mL of BH$_3$.SMe$_2$ (FW: 75.97, 43.55 mmol, 3.6 equiv.) was charged. The batch was warmed to room temperature, then heated to reflux for 22 hours until HPLC analysis indicated only 1.7 A % of starting material remaining. The batch was cooled down to room temperature and quenched by charging 20 mL of saturated NH$_4$Cl aqueous solution. The resultant reaction mixture was concentrated under vacuum to remove the organic solvent. The residue was diluted with 200 mL of ethyl acetate, and extracted with 3×60 mL of 1N HCl aqueous solution. The combined aqueous layers were basified with 50 mL of ammonium hydroxide aqueous solution, and back-extracted with 2×50 mL of methylene chloride. After partition, the organic layer was concentrated to dryness to afford 1.432 g of Compound XI as hemi-solidified liquid, representing a 66% yield in 98.6 A % purity. 1H NMR (CDCl$_3$, 400 MHz): δ=1.02 (d, J=6.8 Hz, 6H), 2.04-2.11 (m, 1H), 3.71 (d, J=6.8 Hz, 2H), 3.79 (s, 2H), 6.87 (dd, J=2.0, 6.8 Hz, 2H), 7.20-7.22 (m 2H).

Example 14: Preparation of Compound Y

To a 50 mL, single neck, round bottom flask, equipped with a stir bar, thermocouple and nitrogen sweep, was charged 500 mg of Compound XI (FW: 179.3, 2.79 mmol, 1.0 equiv.) and 5 mL (10 vol.) of THF. After cooling to 0-5° C., 618.3 mL of 4-nitrophenyl chloroformate (FW: 201.57, 3.07 mmol, 1.1 equiv.) was charged, following by 0.58 mL of Et$_3$N (FW: 101.19, 4.19 mmol, 1.5 equiv.). The batch was warmed to room temperature and stirred at the same temperature for 1 hour until the slurry was too thick to stir. Additional 5 mL (10 vol.) of CH$_2$Cl$_2$ was charged. HPLC analysis indicated 0.82 A % of starting material remaining. The reaction was quenched with 10 mL (20 vol.) of DI water. After partition, the product was in bottom organic layer, which was washed with 10 mL (20 vol.) of saturated NaHCO3 aqueous solution, dried over anhydrous sodium sulfate, and concentrated to dryness in vacuo. The residue was re-dissolved in 10 mL (20 vol.) of CH$_2$Cl$_2$ after heating to reflux, following by charging with 20 mL of heptanes (40 vol.). The product precipitated and the slurry was stirred at room temperature overnight. The product was collected by vacuum filtration, and the filter cake was washed with 2×5 mL (10 vol.) of heptanes, affording 626.8 mg of compound Y as a light yellow solid, representing a 65.3% yield in 91.7 A % purity. 1H NMR (CDCl$_3$, 400 MHz): δ=1.03 (d, J=6.8 Hz, 6H), 2.05-2.12 (m, 1H), 3.72 (d, J=6.8 Hz, 2H), 4.40 (d, J=5.6 Hz, 2H), 5.36 (brs, 1H), 6.90 (d, J=8.4 Hz, 2H), 7.26 (d, J=8.8 Hz, 2H), 7.32-7.35 (m, 2H), 8.24-8.26 (m 2H).

Example 15: Preparation of Compound A from Compound Y

To a 25 mL seal tube, equipped with a stir bar, was charged 344.4 mg of compound Y (FW: 344.4, 1.0 mmol, 1.0 equiv.), 12.2 mg of DMAP (FW: 122.17, 0.1 mmol, 0.1 equiv.), and 2 mL (5.9 vol.) of CH$_3$CN. The tube was sealed and stirred at room temperature for 5 minutes to afford a yellow slurry, which was charged 0.21 mL of (iPr)$_2$NEt (FW: 129.24, 1.2 mmol, 1.2 equiv.). The mixture was heated to 60° C. for 1 hour until HPLC analysis indicated complete reaction. The batch was cooled to room temperature, and concentrated to dryness in vacuo. The residue was dissolved in 5 mL (14.5 vol.) of iPrOAc, and washed with 3×5 mL (14.5 vol.) of NaHCO$_3$ saturated aqueous solution. The product stayed in the upper organic phase, which was dried over anhydrous sodium sulfate, and concentrated again to dryness, and used in the salt formation without further purification.

Example 16: Preparation of Hemi-Tartrate Salt of Pimavanserin

To a 25 mL seal tube, equipped with a stir bar, was charged 344.4 mg of the above crude PMV (1.0 mmol in theory), 75 mg of L-tartaric acid (FW: 150.09, 0.5 mmol, 0.5 equiv.), and 7 mL (16.4 vol.) of absolute ethanol. The tube was sealed and heated to 70° C. to afford a clear solution, then cooled down gradually to room temperature. The product precipitated, and the batch was further cooled down to 0-5° C. and stirred at this temperature for 0.5 hour. The product was collected by vacuum filtration, and the filter cake was washed with 2×1 mL (2.3 vol.) of EtOH. The product was dried in the Buchner funnel under vacuum overnight, affording 177.6 mg of salt, representing a 35.4% yield in 99.6 A % purity. 1H NMR (CDCl$_3$, 400 MHz): δ=1.01 (d, J=6.4 Hz, 6H), 1.79-1.82 (m, 2H), 2.02-2.19 (m, 3H), 2.63 (brs, 5H), 3.38-3.47 (m, 2H), 3.67 (d, J=6.4 Hz, 2H), 4.25 (d, J=4.8 Hz, 2H), 4.32 (s, 1H), 4.38 (s, 2H), 4.58 (brs, 2H), 6.77 (d, J=8.0 Hz, 2H), 6.95-6.99 (m, 4H), 7.17 (d, J=7.2 Hz, 2H).

Example 17: Preparation of Pimavanserin, Via Compound VI-a

To a 25 mL seal tube, equipped with a stir bar, was charged 356.7 mg of CDI (FW: 162.15, 2.2 mmol, 1.1 equiv.) and 4.4 mL (12 vol.) of mixed solvent of $CH_3CN/DMF$ (9/3 vol.). The tube was sealed and stirred at room temperature to obtain a slurry. This was followed by charging a solution of 360 mg (FW: 179.3, 2.0 mmol, 1.0 equiv.) of Compound XI in 3.4 mL (9.4 vol.) of mixed solvent of $CH_3CN/DMF$ (3/1) at room temperature. The batch was stirred at the same temperature for 1 hour until HPLC analysis indicated complete reaction.

The above reaction mixture was charged into the other 25 mL seal tube containing 489.1 mg of Compound V (FW: 222.3, 2.2 mmol, 1.1 equiv.). After sealing the tube, the reaction mixture was heated to 60° C. The batch was stirred at the same temperature for additional 2 hours until HPLC indicated a complete reaction. The reaction mixture was cooled to room temperature, and concentrated to dryness in vacuo. The residue was dissolved in 5 mL of iPrOAc, washed with 5 mL of DI water. After partition, the product was in upper organic layer, which was washed with additional 5 mL of DI water. The resultant organic layer was concentrated again to dryness. The residue was dissolved in 2 mL of iPrOAc after heating to 80° C. to afford a clear solution, which was cooled to room temperature and seeded with a small amount of Pimavanserin. The product precipitated. Additional 8 mL of heptanes was charged, and the slurry was stirred at room temperature for 1 hour and cooled down to 0-5° C. The batch was stirred at the same temperature for additional 1 hour before filtering on a Buchner funnel under vacuum. The filter cake was washed with 2×2 mL of heptanes, and dried in funnel for 2 hours under vacuum, affording 704.3 mg of Pimavanserin, representing a 82.2% yield in 98.5 A % purity.

Example 18: Preparation of Compound VI-a (Isolated)

To a 100 mL, single neck, round bottom flask, equipped with a stir bar, thermocouple and nitrogen sweep, was charged 1.0 g of Compound XI (FW: 179.3, 5.58 mmol, 1.0 equiv.), 0.995 g of CDI (FW: 162.15, 6.13 mmol, 1.1 equiv.) and 10 mL (10 vol.) of $CH_3CN$. The mixture was stirred at room temperature for 1 hour until HPLC indicated only 1.0 A % of starting material remaining. The batch was concentrated to dryness. The residue was purified by silica gel chromatography, eluting with 0-10% of MeOH in $CH_2Cl_2$, affording 1.44 g of compound VI-a as a low melting point white solid, representing a 94.7% yield in 97.8 A % purity. $^1H$ NMR ($CDCl_3$, 400 MHz): δ=1.02 (d, J=6.4 Hz, 6H), 2.02-2.12 (m, 1H), 3.70 (d, J=6.8 Hz, 2H), 4.50 (d, J=5.6 Hz, 2H), 6.87 (d, J=8.8 Hz, 2H), 6.95 (s, 1H), 7.10 (brs, 1H), 7.24 (d, J=8.8 Hz, 2H), 7.37-7.38 (m, 1H), 8.08 (s, 1H).

Example 19: Preparation of Pimavanserin Via Isolated Compound VI-a

To a 25 mL seal tube, equipped with a stir bar, was charged with 597 mg of compound VI-a (FW: 273.15, 2.2 mmol, 1.0 equiv.), following by a solution of 534.5 mg (FW: 222.3, 2.4 mmol, 1.1 equiv.) of Compound V in 6 mL of $CH_3CN$. After sealing the tube, the reaction mixture was heated to 60° C. The batch was stirred at the same temperature for additional 1 hour until HPLC indicated a complete reaction. The reaction mixture was cooled to room temperature, and concentrated to dryness in vacuo. The residue was dissolved in 4 mL (7.5 vol.) of iPrOAc after heating to 80° C. to afford a clear solution, which was cooled to room temperature and seeded with a small amount of Pimavanserin. The product precipitated, the slurry was stirred at room temperature overnight. The batch was diluted with 2 mL (2.5 vol.) of iPrOAc, and filtered under vacuum. The filter cake was washed with additional 2 mL of (2.5 vol.) of iPrOAc, and dried in the funnel under vacuum for 0.5 hour, affording 290.9 mg of Pimavanserin as white solid, representing a 31.1% yield in 99.3 A % purity.

Example 20: Comparative Example: Coupling of Carbamate Derivative to a Secondary Amine

Step 1: Synthesis of 4-nitrophenyl 4-fluorobenzyl(1-methylpiperidin-4-yl)carbamate To a 250 mL, single neck, round bottom flask, equipped with a stir bar, thermocouple and nitrogen sweep, was charged 0.923 g of Compound V (FW: 222.3, 4.17 mmol, 1.0 equiv.). This was followed by charge of 8 mL (8.6×) of dichloromethane, and 0.87 mL of $Et_3N$ (FW: 101.19, 6.3 mmol, 1.5 equiv.). The mixture was stirred at room temperature for 5 minutes, then cooled down to 0-5° C. At this temperature, 0.93 g (FW: 201.57, 4.6 mmol, 1.1 equiv.) of 4-nitrophenyl chloroformate in 2 mL of $CH_2Cl_2$ was charged dropwise. The batch was warmed to room temperature and stirred at the same temperature for 1 hour before quenching with 50 ml of DI water. After partition, the product in bottom organic layer was washed with 2×50 mL of NaHCO3 saturated aqueous solution, and concentrated to dryness in vacuo. The residue was purified by silica gel chromatography, eluting with 50% of ethyl acetate in heptanes. The crude product was collected and purified again by silica gel chromatography, eluting with 10% MeOH in methylene chloride to afford 1.36 g of product as a yellow oil, representing a 82.8% yield. 1H NMR ($CDCl_3$, 400 MHz): δ=1.75-1.98 (brm 4H), 2.00-2.06 (m, 2H), 2.27 (s, 3H), 2.88-2.91 (m, 2H), 3.95-4.16 (brm, 1H), 4.55-4.59 (m, 2H), 7.02-7.19 (m, 2H), 7.17-7.36 (s, 4H), 8.21-8.28 (m, 2H).

Step 2: Synthesis of Pimavanserin by Coupling Between 4-nitrophenyl 4-fluorobenzyl(1-methylpiperidin-4-yl)carbamate and Compound XI To a 20 mL vial, was charged with 0.319 g of 4-nitrophenyl 4-fluorobenzyl(1-methylpiperidin-4-yl)carbamate (FW: 389.42, 0.82 mmol, 1.0 equiv.) and a solution of 0.15 g of Compound XI (FW: 179.26, 0.84 mmol, 1.02 equiv.) in 2 mL of DMF. This was followed by the charge of 0.17 mL of $(iPr)_2NEt$ (FW: 129.24, 0.96 mmol, 1.17 equiv.), and 9.8 mg of DMAP (FW: 122.17, 0.08 mmol, 0.1 equiv.). The reaction mixture was heated to 100° C., and stirred at the same temperature for approximately 16 hours. LC-MS indicated 9.8 A % of Pimavanserin was present in the crude reaction mixture. HRMS-ESI (m/z): [M+1]+ Calcd for $C_{25}H_{35}F_1N_3O_2$: 428.2708; found 428.2701.

Step 3: Synthesis of Compound VI

To a 50 mL, single neck, round bottom flask, equipped with a stir bar, thermocouple and nitrogen sweep, was charged 444.6 mg of Compound V (FW: 222.3, 2.0 mmol, 1.0 equiv.), and 4.5 mL (10 vol.) of dichloromethane. This was followed by the charge of 729.7 mg of CDI (FW: 162.1, 3.0 mmol, 1.5 equiv.), and 0.56 mL of Et3N (FW: 101.19, 4.0 mmol, 2.0 equiv.) at room temperature. The reaction was monitored by TLC, and stirred at room temperature until no limiting starting material remaining. The batch was quenched with 15 ml of DI water, extracted with 2×15 mL of dichloromethane. The organic layers were combined and concentrated to dryness in vacuo. The residue was purified by silica gel chromatography, eluting with 0-10% of MeOH in $CH_2Cl_2$ in the presence of 2% of NH3.H2O to afford 229.6 mg of compound VI, representing a 36.2% yield in >90% purity. $^1$H NMR (CDCl$_3$, 400 MHz): δ=1.76-1.78 (m 2H), 1.92-19.8 (m, 4H), 2.25 (s, 3H), 2.88-2.91 (m, 2H), 3.78-3.94 (brm, 1H), 4.58 (s, 2H), 7.01-7.06 (m, 2H), 7.12 (s, 1H), 7.17-7.18 (m, 1H), 7.21-7.25 (m, 2H), 7.87-7.88 (m, 1H).

Step 4: Synthesis of Pimavanserin by Coupling Between Compound VI and Compound XI To a 10 mL seal tube, was charged 130 mg of Compound XI (FW: 175.26, 0.73 mmol, 1.0 equiv.), DMAP (FW: 122.17, 0.88 mmol, 1.2 equiv.). This was followed by the charge of a solution of 229.6 mg of compound VI (FW: 316.37, 0.73 mmol, 1.0 equiv.) in 2.3 mL of DMF at room temperature. The mixture was heated to 100° C. and stirred at the same temperature for 17 hours. HPLC indicated 3.7 A % of pimavanserin was present in the crude reaction mixture, while the major product was impurity compound, 1,3-bis(4-isobutoxy-benzyl)urea, at 58.7 A %.

Example 21: Preparation of Pimavanserin Via Compound V as Dihydrochloride Salt

Step 1: Preparation of N-(4-fluorobenzyl)-1-methylpiperidin-4-amine Dihydrochloride (Compound V×2HCl)

The reaction was performed in 300 mL reactor. The reactor was purged with $N_2$, then Argon. 4-Fluorobenzylamine (10 g; 80 mmol, 1.0 eq) was dissolved in dry MeCN (100 mL), then 1-methylpiperidin-4-one (10.9 g; 96 mmol, 1.2 eq) was added and the reaction mixture was stirred at ambient temperature for 18 h. Then, the reaction mixture was cooled to 0° C. and 25.4 g of NaBH(OAc)$_3$ (25.4 g; 120 mmol, 1.5 eq) was added in portions over 20 min and the reaction was allowed to stir to room temperature. After 1 h, the reaction was quenched by the addition of 200 ml of water, pH was adjusted to 2 with 5M HCl and then extracted using 3×250 mL of DCM. Basification of the aqueous layer to pH 9.5 with 30% sol. NaOH and extraction 3×300 ml of DCM followed. The organic layers were collected and dried over anh. Na$_2$SO$_4$, filtered and evaporated to dryness yielding 17.24 g (92%) of oily product, N-(4-fluorobenzyl)-1-methylpiperidin-4-amine (Compound V).

To a 250 mL, three necked, round bottom flask, equipped with a stir bar and thermometer, N-(4-fluorobenzyl)-1-methylpiperidin-4-amine (10 g; 0.045 mol) and DCM (50 mL) were charged and cooled to 10-15° C. To the resulting solution, 5-6 N HCl in 2-PrOH (3 equiv., 0.135 mmol) was added dropwise over 25 min., white crystals formed, and the solution then cooled to 0-5° C. for 2 hours. Crystals were filtered off, washed with 50 mL of DCM, dried at 50° C./10 mbar for 10 hours yielding 12.8 g (96.4%) of N-(4-fluorobenzyl)-1-methylpiperidin-4-amine dihydrochloride (Compound V×2HCl).

Step 2: Preparation of 4-isobutoxybenzaldehyde (Compound XIII)

4-Hydroxybenzaldehyde (10 g; 0.082 mol), potassium carbonate (33.95 g; 0.246 mol) and potassium iodide (1.36 g; 0.008 mol) were suspended in N,N-dimethylformamide (50 mL). Isobutyl bromide (26.7 mL; 0.246 mol) was added and the reaction was heated at 70° C. under nitrogen for 3 hours. The reaction was cooled down, diluted by using 150 mL of water and extracted by using 300 mL of ethyl acetate. The organic layer was extracted five times by using 150 mL of 10% NaCl solution, dried under Na$_2$SO$_4$, filtered and concentrated which resulted in 14.3 g (98%) of yellow oily product of 4-isobutoxybenzaldehyde (Compound XIII).

Step 3: Preparation of (4-isobutoxyphenyl)methanamine hydrochloride (Compound XI×HCl)

To a solution of 4-isobutoxybenzaldehyde (Compound XIII) (19.9 g; 0.112 mol) in methanol (90 mL), Raney nickel (6 g) and 7N methanol ammonia solution (90 mL) were added. The reaction mixture was stirred under hydrogen atmosphere (0.5 bar) at 10-15° C. for 24 hours. The reaction solution was filtered through Celite to remove the catalyst. Methanol was distilled off and toluene (500 mL) was added. The solution was concentrated to 250 mL and 5-6 N HCl in 2-PrOH (30 mL; 0.15 mol) was added dropwise at ambient temperature. The resulting suspension was then cooled to 5° C. and stirred for additional 2 hours. Crystals were filtered off, washed with 60 mL of toluene, dried at 50° C./10 mbar for 10 hours yielding 20.88 g (86.7%) of (4-isobutoxyphenyl)methanamine hydrochloride (Compound XI×HCl). The product was analyzed by PXRD—form I was obtained, the PXRD pattern is shown in FIG. 3.

Step 4: Option 1: Preparation of 1-(4-fluorobenzyl)-3-(4-isobutoxybenzyl)-1-(1-methylpiperidin-4-yl) urea (Pimavanserin Part a: Preparation of Compound VI-a:

To a 250 mL, three necked, round bottom flask, equipped with a stir bar, condenser and thermometer, (4-isobutoxyphenyl)methanamine hydrochloride (Compound XI×HCl) (5 g, 0.023 mol), CDI (6.01 g; 0.037 mol) and acetonitrile (40 mL) were charged. The resulting solution was stirred for 1 h at 65-70° C. and monitored by HPLC until full conversion to Compound VI-a.

Part b: Preparation of Pimavanserin:

N-(4-fluorobenzyl)-1-methylpiperidin-4-amine (Compound V) (7.73 g; 0.035 mol) was added to Compound VI-a obtained above. After 2 h, complete conversion was observed. Upon completion, the reaction solution was cooled to 50° C. and water was added dropwise in a 1:3 ratio (120 mL). After addition of a whole amount of water, crystals were formed and suspension was allowed to cool to ambient temperature. The crystals were filtered off, washed with 2×40 mL solution of CH$_3$CN:H$_2$O 1:3, then 40 mL of water, dried at 45° C./10 mbar for 10 hours yielding 9.35 g (94.4%) of 1-(4-fluorobenzyl)-3-(4-isobutoxybenzyl)-1-(1-methylpiperidin-4-yl)urea (Pimavanserin).

Step 4—Option 2: Preparation of 1-(4-fluorobenzyl)-3-(4-isobutoxybenzyl)-1-(1-methylpiperidin-4-yl)urea (Pimavanserin)

Part a: Preparation of Compound VI-a:

To a 500 mL, three necked, round bottom flask, equipped with a stir bar, condenser and thermometer, (4-isobutoxyphenyl)methanamine hydrochloride (Compound XI×HCl) (10 g; 0.046 mol), CDI (11.28 g; 0.07 mol) and acetonitrile (100 mL) were charged. The resulting solution was stirred for 1 h at 65-70° C. and monitored by HPLC until full conversion to Compound VI-a.

Part b: Preparation of Pimavanserin:

The reaction solution containing Compound VI-a obtained above was cooled to 30° C. and N-(4-fluorobenzyl)-1-methylpiperidin-4-amine dihydrochloride (Compound V×2HCl) (20.53 g; 0.07 mol) and $K_2CO_3$ (9.61 g; 0.07 mol) were added. The reaction mixture was heated to 65-70° C. and stirred for next 18 hours. Upon completion, the reaction solution was cooled to 50° C., pH of solution was adjusted to 10.5 with 6N NaOH solution, and water was added dropwise in ratio 1:3 (300 mL). After addition of a whole amount of water, crystals were formed, and suspension was allowed to cool to ambient temperature, and then cooled on ice-bath (0-5° C.) for 1.5 hour. The crystals were filtered off, washed with 2×100 mL solution of $CH_3CN:H_2O$ 1:3, then 100 mL of water, dried at 45° C./10 mbar for 10 hours yielding 18.797 g (95.6%) of 1-(4-fluorobenzyl)-3-(4-isobutoxybenzyl)-1-(1-methylpiperidin-4-yl)urea (Pimavanserin).

Example 22: Preparation of Crystalline Form I of N-(4-fluorobenzyl)-1-methylpiperidin-4-amine Dihydrochloride (Compound V×2HCl)

The reaction was performed in 250 mL, three necked, round bottom flask. 4-Fluorobenzylamine (11.010 g; 88 mmol, 1.0 eq) was dissolved in dry MeCN (110 mL), 1-methylpiperidin-4-one (10.5 g; 92 mmol, 1.05 eq) was added and the reaction mixture was stirred at ambient temperature for 16 h. Then, the reaction mixture was cooled to 0° C., $NaBH(OAc)_3$ (29.8 g; 140 mmol, 1.6 eq) was added and the reaction mixture was allowed to stir to room temperature. After 3 h, the reaction was quenched by addition of 250 ml of water; pH was adjusted to 2 with 2M HCl extracted 3×250 mL of ethyl acetate, followed by basification of aqueous layer to pH 9.5 with 40% sol. NaOH and extraction 3×200 ml of ethyl acetate. The organic layers were collected and dried over anh. $Na_2SO_4$, filtered and evaporated to dryness yielding 17.24 g (86.96%) of oily product, N-(4-fluorobenzyl)-1-methylpiperidin-4-amine (Compound V).

To a 250 mL, three necked, round bottom flask, equipped with a stir bar and thermometer, N-(4-fluorobenzyl)-1-methylpiperidin-4-amine (17.01 g; 0.077 mol) and ethyl acetate (170 mL) were charged and cooled to 10-15° C. To the resulting solution, 5-6 N HCl in 2-PrOH (3.4 equiv., 0.264 mol) was added dropwise over 25 min, white crystals formed, and the solution then cooled to 0-5° C. for 2 hours. Crystals were filtered off, washed with 100 mL of ethyl acetate, dried at 50° C./10 mbar for 10 hours yielding 20.4 g (89.75%) of N-(4-fluorobenzyl)-1-methylpiperidin-4-amine dihydrochloride (Compound V×2HCl). The product was analyzed by PXRD—form I was obtained.

Example 23: Preparation of Crystalline Form I of N-(4-fluorobenzyl)-1-methylpiperidin-4-amine Dihydrochloride (Compound V×2HCl)

The reaction was performed in 250 mL, three necked, round bottom flask. 4-Fluorobenzylamine (11.010 g; 88 mmol, 1.0 eq) was dissolved in dry MeCN (110 mL), 1-methylpiperidin-4-one (10.5 g; 92 mmol, 1.05 eq) was added and the reaction mixture was stirred at ambient temperature for 16 h. Then, the reaction mixture was cooled to 0° C., $NaBH(OAc)_3$ (29.8 g; 140 mmol, 1.6 eq) was added and the reaction mixture was allowed to stir to room temperature. After 3 h, the reaction was quenched by addition of 250 ml of water; pH was adjusted to 2 with 2M HCl, extracted 3×250 mL of DCM, followed by basification of aqueous layer to pH 9.5 with 40% sol. NaOH, and extraction using 3×200 ml of DCM. Organic layers were collected and dried over anh. $Na_2SO_4$, filtered and evaporated to dryness yielding 17.52 g (89.57%) of oily product, N-(4-fluorobenzyl)-1-methylpiperidin-4-amine (Compound V).

To a 250 mL, three necked, round bottom flask, equipped with a stir bar and thermometer, N-(4-fluorobenzyl)-1-methylpiperidin-4-amine (17.52 g; 0.079 mol) and DCM (100 mL) were charged and cooled to 10-15° C. To the resulting solution, 5-6 N HCl in 2-PrOH (3.3 equiv., 0.264 mol) was added dropwise over 25 min, white crystals formed, and the solution then cooled to 0-5° C. for 2 hours. Crystals were filtered off, washed with 100 mL of DCM, dried at 50° C./10 mbar for 10 hours yielding 21.93 g (94.24%) of N-(4-fluorobenzyl)-1-methylpiperidin-4-amine dihydrochloride (Compound V×2HCl). The product was analyzed by PXRD—form I was obtained, the PXRD pattern is shown in FIG. 1.

Example 24: Preparation of Crystalline Form II of N-(4-fluorobenzyl)-1-methylpiperidin-4-amine Dihydrochloride (Compound V×2HCl)

The reaction was performed in a 250 mL, three necked, round bottom flask. 4-Fluorobenzylamine (11.010 g; 88 mmol, 1.0 eq) was dissolved in dry MeCN (110 mL), 1-methylpiperidin-4-one (10.5 g; 92 mmol, 1.05 eq) was added and the reaction mixture was stirred at 40° C. for 16 h. Then, the reaction mixture was cooled to 0° C., $NaBH(OAc)_3$ (29.8 g; 140 mmol, 1.6 eq) was added and the reaction mixture was allowed to stir to room temperature. After 3 h, the reaction was quenched by addition of 250 ml of water; pH was adjusted to 2 with 2M HCl and then extracted using 3×250 mL of DCM. Basification of the aqueous layer to pH 9.5 with 40% sol. NaOH and extraction using 3×200 ml of DCM followed. The organic layers were collected and dried over anh. $Na_2SO_4$, filtered and evaporated to dryness yielding 16.83 g (86.04%) of oily product, N-(4-fluorobenzyl)-1-methylpiperidin-4-amine (Compound V).

To a 250 mL, three necked, round bottom flask, equipped with a stir bar and thermometer, N-(4-fluorobenzyl)-1-methylpiperidin-4-amine (16.83 g; 0.076 mol) and DCM (100 mL) were charged and cooled to 10-15° C. To the resulting solution, 4.395 N HCl in 2-PrOH (3.5 equiv., 0.264 mol) was added dropwise over 25 min, white crystals was formed, and the solution then cooled to 0-5° C. for 2 hours. Crystals were filtered off, washed with 100 mL of DCM, dried at 50° C./10 mbar for 10 hours yielding 19.89 g (88.99%) of N-(4-fluorobenzyl)-1-methylpiperidin-4-amine dihydrochloride (Compound V×2HCl). The product was analyzed by PXRD—form II was obtained.

Example 25: Preparation of Crystalline Form II of N-(4-fluorobenzyl)-1-methylpiperidin-4-amine Dihydrochloride (Compound V×2HCl)

The reaction was performed in a 1000 mL reactor. N-(4-fluorobenzyl)-1-methylpiperidin-4-amine (100 g, 0.45 mol) and DCM (500 mL) were charged and cooled to 10-15° C. To the resulting solution, 5-6 N HCl in 2-PrOH (3 equiv., 1.35 mol) was added dropwise over 25 min, white crystals was formed, and the solution then cooled to 0-5° C. for 2 hours. Crystals were filtered off, washed with 200 mL of DCM, dried at 50° C./10 mbar for 20 hours yielding 127.74 g (96.15%) of N-(4-fluorobenzyl)-1-methylpiperidin-4-amine dihydrochloride (Compound V×2HCl). The product was analyzed by PXRD—form II was obtained, the PXRD pattern is shown in FIG. 2.

Example 26: One Pot Preparation of Pimavanserin (Without Isolation of Compound 1)

Step 1: Preparation of 2-(4-isobutoxyphenyl)acetic acid

To a 250 mL, 3 neck, round bottom flask, equipped with thermocouple and nitrogen sweep, was charged 10 g of 4-hydroxy phenyl acetic acid (Molecular weight (FW): 152.15, 65.7 mmol, 1.0 equiv.), 30 g of potassium carbonate (FW: 138.21, 216.8 mmol, 3.3 equiv.), 1.1 g of potassium iodide (KI, FW: 166, 6.57 mmol, 0.1 equiv.), followed by 100 mL (10 vol.) of DMF. After stirring for 5 minutes at room temperature, 15.7 mL of isobutyl bromide (FW: 137.02, 144.6 mmol, 2.2 equiv.) was charged into the batch. The mixture was then heated to 75° C. and kept stirring at the same temperature for 2 days until no limited starting material remaining as determined by HPLC. The reaction was cooled down to room temperature, and quenched by charging with 100 mL of deionized (DI) water. The pH of the reaction mixture was adjusted to less than 1 by charging 100 mL of 2N HCl. The product was extracted with 150 mL of ethyl acetate. After partitioning, the upper organic layer was washed with additional 100 mL of DI water, concentrated to dryness on the rotary evaporator under vacuum. The residue was dissolved in 100 mL each of THF (10 vol) and DI water (10 vol). After charging 20 g of lithium hydroxide, the mixture was heated to reflux for 3 hours until complete reaction. The batch was cooled to room temperature, concentrated on rotary evaporator to remove THF. The residue was acidified with 300 mL of 2N HCl and 45 mL of 6N HCl aqueous solution until pH<1. The product was extracted with 2×250 mL of methylene chloride, dried over sodium sulfate, and filtered on Buchner funnel. The filtrate was concentrated to dryness on rotary evaporator under vacuum to afford 10.18 g of 2-(4-isobutoxyphenyl)acetic acid, representing a 74.4% yield in 98.5 A % purity. $^1$H NMR (d$_6$-DMSO, 400 MHz): δ=0.97 (d, J=6.8 Hz, 6H), 1.96-2.02 (m, 1H), 3.47 (s, 2H), 3.71 (d, J=6.4 Hz, 2H), 6.86 (d, J=8.8 Hz, 2H), 7.14 (d, J=8.8 Hz, 2H).

Step 2: Preparation of Pimavanserin

To a 50 mL, single neck, round bottom flask, equipped with thermocouple and nitrogen sweep, was charged 333.2 mg of 2-(4-isobutoxyphenyl)acetic acid (FW: 208.25, 1.6 mmol, 1.0 equiv.), 311.3 mg of CDI (FW: 162.15, 1.92 mmol, 1.2 equiv.), and 3.3 mL of CH$_3$CN (10 vol.). After stirring at room temperature for 1 hour, this was charged 139 mg (FW: 69.5, 2.0 mmol, 1.25 equiv.) of NH$_2$OH HCl and stirred for additional 15-18 hours at room temperature. Additional 518.9 mg of CDI (FW: 162.15, 3.2 mmol, 2.0 equiv.) was charged and the batch turned from a slurry to a clear solution again. This was followed by charging a solution of 334 mg of Compound V (FW: 222.3, 1.5 mmol, 0.94 equiv.), and heating up to 60° C. The reaction was stirred at this temperature for approximately 5 hour before cooling back to room temperature. The reaction was quenched with 20 mL of DI water, and concentrated on rotary evaporator to remove acetonitrile. The aqueous residue was diluted with 40 mL of ethyl acetate, and washed with 2×20 mL of brine. The organic phase was concentrated to dryness on rotary evaporator under vacuum. The residue was purified by chromatography (160 g RediSep Alumina column), eluting with 0-5% of methanol in dichloromethane to afford 305 mg of Pimavanserin, representing a 47.6% yield in 99.3 A % purity. $^1$H NMR (CDCl$_3$, 400 MHz): δ=1.01 (d, J=6.8 Hz, 6H), 1.62-1.73 (m, 4H), 2.03-2.09 (m, 3H), 2.25 (s, 3H), 2.84-2.87 (m, 2H), 3.68 (d, J=6.4 Hz, 2H), 4.27-4.34 (m, 5H), 4.45-4.48 (m, 1H), 6.67-6.79 (m, 2H), 6.99-7.02 (m, 4H), 7.16-7.27 (m, 2H). HRMS-ESI (m/z): [M+1]$^+$ Calcd for C$_{25}$H$_{35}$F$_1$N$_3$O$_2$: 428.2708; found 428.2723.

Example 27: Preparation of Pimavanserin (with Isolation of Compound 1)

Step 1: Preparation of Compound 1

To a 100 mL, single neck, round bottom flask, equipped with thermocouple and nitrogen sweep, was charged 1 g of Compound XV (FW: 208.25, 4.8 mmol, 1.0 equiv.), 934.0 mg of CDI (FW: 162.15, 5.76 mmol, 1.2 equiv.), followed by 10 mL (10 vol.) of acetonitrile. After stirring for 45 minutes at room temperature, 417 mg of NH$_2$OH.HCl (FW: 69.5, 6.0 mmol, 1.25 equiv.) was charged into the batch. The mixture was kept stirring at the ambient temperature overnight and turned into a thick slurry. HPLC determined 1.6 A % of starting material remaining. The batch was diluted with 6 mL of acetonitrile (6 vol.) and 16 mL (16 vol.) of DI water, and cooled down to 0-5° C. After stirring at the same temperature for additional 1 hour, the batch was filtered on the Buchner funnel. The filter cake was washed with 2×10 mL (10 vol.) of DI water, and dried in the funnel under vacuum overnight to afford 774.1 mg of hydroxamic acid Compound 1, representing a 72% yield in 99.6 A % purity. $^1$H NMR (CDCl$_3$, 400 MHz): δ=0.96 (d, J=6.8 Hz, 6H), 1.95-2.02 (m, 1H), 3.19 (s, 2H), 3.70 (d, J=6.4 Hz, 2H), 6.85 (d, J=8.4 Hz, 2H), 7.14 (d, J=8.4 Hz, 2H), 8.80 (s, 1H), 10.61 (s, 1H).

Step 2: Synthesis of Pimavanserin

To a 50 mL sealed tube, equipped with nitrogen sweep, was charged 250 mg of compound 1 (FW: 223.27, 1.12 mmol, 1.0 equiv.), 217.9 mg of CDI (FW: 162.15, 1.34 mmol, 1.2 equiv.), and 1.7 mL of acetonitrile (6.8 vol.). After stirring at room temperature for 40 minutes, the batch was heated to 60° C. and kept stirring at the same temperature for additional 10 minutes. This was followed by charging 373.5 mg of Compound 3 (FW: 222.3, 1.68 mmol, 1.5 equiv.). The container of Compound V was rinsed with 0.5 mL (2 vol.) of acetonitrile, and the wash was combined with the batch. The reaction was monitored by HPLC and complete in 2 hours. The batch was cooled down to room temperature, diluted with 5 mL (20 vol.) of ethyl acetate, which was washed with 3×5 mL (20 vol.) of DI water. After partitioning, the upper organic layer was concentrated to dryness on rotary evaporator. The residue was re-dissolved into 3 mL (12 vol.) of ethyl acetate after heating up to reflux to afford a slightly milky solution. This was charged with 12 mL (48 vol.) of heptane, and cooled down to 0-5° C. The batch was kept stirring at the same temperature for 1 hour and filtered on a Buchner funnel. The filter cake was washed with 2×5 mL (20 vol.) of heptane, and dried in the funnel with a nitrogen sweep for 1 hour to afford 270.8 mg of Pimavanserin as a white solid, representing a 56.6% yield in 98.8 A % purity. $^1$H NMR (CDCl$_3$, 400 MHz): δ=1.01 (d, J=6.8 Hz, 6H), 1.62-1.73 (m, 4H), 2.03-2.09 (m, 3H), 2.25 (s, 3H), 2.84-2.87 (m, 2H), 3.68 (d, J=6.4 Hz, 2H), 4.27-4.34 (m, 5H), 4.45-4.48 (m, 1H), 6.67-6.79 (m, 2H), 6.99-7.02 (m, 4H), 7.16-7.27 (m, 2H). HRMS-ESI (m/z): [M+1]$^+$ Calcd for C$_{25}$H$_{35}$F$_1$N$_3$O$_2$: 428.2708; found 428.2723.

Example 28: Preparation of Compound V

The reaction was performed in a 300 mL reactor. The reactor was purged with N$_2$, then Ar. 10 g of 4-fluorobenzylamine (FW: 125.14, 79.91 mmol, 1.0 equiv) was dissolved in 100 ml of dry MeCN (10 vol.), then 1-methylpiperidin-4-one (FW: 113.16, 95.97 mmol, 1.2 equiv) was added and the reaction mixture was stirred at ambient temperature for 18 h. Then, the reaction mixture was cooled to 0° C., and 25.4 g of NaBH(OAc)$_3$ (FW: 119.85 mmol, 1.5 equiv) was added in portions over 20 min. The reaction was allowed to stir to room temperature. After 1 h, according HPLC and TLC (system of solvents: DCM:MeOH:NH$_4$OH 90:9:1.5), complete conversion was observed. The reaction was quenched by addition of 200 ml of water (20 vol.), pH was adjusted to 2 with 5M HCl and then extracted using 3×250 ml of DCM (3×25 vol.) to remove impurities. Basification to pH 9.5 with 30% sol. NaOH, and extraction 3×300 ml of DCM (3×30 vol.) was then performed. Extraction was monitored by TLC. Organic layers were collected and dried over anh. Na$_2$SO$_4$, filtered and evaporated to dryness yielding 17.24 g of oily product, Compound V, HPLC purity 95% (yield 92%).

Example 29: Preparation of Compound 1 in a Crystalline Form I

The solution of Compound 1 (1 g) in MeOH (7.5 mL) was stirred at 40° C. and the temperature was gradually lowered during 3 h. A thick suspension was observed, then 5 mL of MeOH was added, stirred for 3 h, filtered, washed with cold MeOH, and dried at 45° C. in vacuum for 3 h to yield 0.152 g of precipitate, HPLC purity 99.2 area %.

Example 30: Preparation of Compound 1 in a Crystalline Form II

To a 250 ml reactor, equipped with mechanical stirrer and thermometer, 10 g of methyl 2-(4-hydroxyphenyl)acetate (FW: 166.17, 0.060 mol, 1.0 equiv), 33.27 g of potassium carbonate (FW: 138.21, 0.241 mol, 4.0 equiv), 1.00 g of KI (FW: 166.00, 0.006 mol, 0.1 equiv) and 50 ml of DMF (5 vol.) was charged. After stirring for 5 minutes at RT, 33 ml of isobutyl bromide (FW: 137.02, 0.301 mol, 5.0 equiv) was added. The mixture was then heated at 70-75° C. for 22 hours until no starting material remained as determined by HPLC. The reaction mixture was cooled to 15° C., diluted with 50 ml of MeOH (5 vol.) and cooled down to 5° C., followed by addition of 37 ml of NH$_2$OH, 50% aq. sol. (10 equiv) and 28 ml of 25% solution of sodium methoxide in MeOH (2 equiv). The mixture was stirred at 5-10° C. for 1 hour. Solid was filtered off and washed with 60 ml of MeOH (6 vol.). The filtrate was transferred to 1 L reactor and pH was adjusted to less than 4.5 by dropwise addition of 315 ml of 2N HCl at RT. Additional 60 ml of water was added dropwise at RT. Resulted suspension was cooled down to 15° C. and stirred for additional 2 hours. Solid was filtered off, washed with water (2×30 ml) and dried in vacuum oven at 40° C. and 710 mbar for 10 hours to afford 11.21 g (83.4% yield) of Compound 1, HPLC purity 98.9 area %.

Example 31: Preparation of Pimavanserin

To a 50 mL, three neck, round bottom flask, equipped with a stir bar and thermometer, Compound 1, 1 g, was charged (FW: 223.27, 4.48 mmol, 1.0 equiv.). This was followed by charging of 10 mL of acetonitrile, anhydrous, 99.8%, and 0.872 g of CDI (FW: 162.15, 5.38 mmol, 1.2 equiv.). The resulting solution was stirred for 2 h at ambient temperature, then heated to 60° C. and the rearrangement monitored by HPLC. Upon full conversion, the amine, Compound V, 1.99 g, (FW: 222.30, 8.95 mmol, 2 equiv) was added. After 45 min, complete conversion was observed. The reaction was monitored by HPLC and TLC (systems of solvents: DCM:MeOH:NH$_4$OH 90:9:1.5 and DCM:MeOH 10:1).

Upon completion, the reaction mixture was divided and worked-up using two different routes.

Work-Up 1:

The reaction mixture was diluted with EtOAc (20 mL) and washed twice with a saturated solution of NH$_4$Cl (2×15 mL), then with a saturated NaCl solution (10 mL). The organic layer was dried over anh. Na$_2$SO$_4$, filtered and evaporated to 5 mL. The solution was stirred at ambient temperature and n-heptane (10 mL) was added dropwise. White precipitate was formed, filtered off, washed with n-heptane and dried at 45° C. in vacuum for 3 h, yielding 0.251 g of Pimavanserin (form Y), HPLC purity 98 area %.

Work-Up 2:

The reaction mixture was diluted with EtOAc (20 mL) and washed three times with 0.1 M HCl (3×15 mL), following with a saturated NaCl solution (10 mL). The organic layer was dried over anh. Na$_2$SO$_4$, filtered and evaporated to 5 mL. The solution was stirred at 60° C. and n-heptane (15 mL) was added dropwise. An oil was first formed, followed by a white precipitate. The temperature was gradually lowered over 3 h, and left to stir overnight. The precipitate was filtered off, washed with n-heptane and dried at 45° C. in vacuum for 3 h, yielding 0.094 g of precipitate HPLC purity 95.3 area %. From the mother liquid, after filtration, washing and drying, 0.046 g of precipitate (form X) was observed, HPLC purity 97.6 area %.

Example 32: Preparation of Pimavanserin—in a Crystalline Form Y

To a 50 mL, three neck, round bottom flask, equipped with a stir bar and thermometer, Compound 1, 1 g, was charged (FW: 223.27, 4.48 mmol, 1.0 equiv.). This was followed by adding 10 mL of acetonitrile, anhydrous, 99.8%, and 0.872 g of CDI (FW: 162.15, 5.38 mmol, 1.2 equiv.). The resulting solution was stirred for 2 h at ambient temperature, heated to 60° C. and the rearrangement monitored by HPLC. Upon full conversion, the amine, Compound V, 1.99 g, (FW: 222.30, 8.95 mmol, 2 equiv.) was added. After 1 h, complete conversion was observed. The reaction was monitored by HPLC and TLC (systems of solvents: DCM:MeOH:NH$_4$OH 90:9:1.5 and DCM:MeOH 10:1).

Upon completion, the reaction was diluted with iPrOAc (20 mL), washed twice with a saturated solution of NH$_4$Cl (2×15 mL), then with H$_2$O (10 mL) and finally with a saturated NaCl solution (10 mL). The organic layer was dried over anh. Na$_2$SO$_4$, filtered and evaporated to 5 mL. The solution was stirred at ambient temperature and n-heptane (20 mL) was added dropwise. White precipitate was formed, then filtered off, washed with n-heptane and dried at 40° C. in vacuum for 3 h, yielding 1.43 g of Pimavanserin, HPLC purity 98.5 area % (yield 75%).

Example 33: Preparation of 3-(4-isobutoxybenzyl)-1,4,2-dioxazol-5-one (Referred to as Compound 2)

To a 50 mL, double neck, round bottom flask, equipped with a stir bar, Compound 1, 1 g, was charged (FW: 223.27, 4.48 mmol, 1.0 equiv.). This was followed by adding 10 mL of acetonitrile, anhydrous, 99.8%, and 0.872 g of CDI (FW: 162.15, 5.38 mmol, 1.2 equiv.). The mixture was stirred at room temperature for 45 minutes. Then, a cold 1 M aqueous solution of HCl (25 mL) was added, and the mixture was extracted with dichloromethane, dried over anh. sodium sulfate and concentrated under reduced pressure to give a crude mixture of product. After the addition of iPrOAc, a white precipitate was observed. Following filtration and drying, 0.413 g of 2a was afforded as a by-product of the reaction. HPLC-MS (m/z) [M+1]$^+$ 274.1; $^1$H NMR (CDCl$_3$, 500 MHz): δ=0.99 (d, J=6.7 Hz, 6H), 1.99-2.09 (m, 1H), 3.65 (d, J=6.5 Hz, 2H), 4.49 (d, J=5.8 Hz, 2H), 6.78-6.86 (m, 2H), 7.34-7.41 (m, 3H), 7.87 (s, 1H), 10.03 (brt, J=5.7 Hz, 1H), 10.36 (s, 1H).

The mother liquid was evaporated to dryness and the product was dissolved in EtOH and left to crystallize. After two days, solvatization of product was observed, followed by trituration with n-heptane. The product was filtered off and dried in vacuum at 45° C. for 2 h to give 0.384 g of 3-substituted-1,4,2-dioxazol-5-one, Compound 2. HPLC-MS (m/z) [M+1]$^+$ 250.1; $^1$H NMR (CDCl$_3$, 400 MHz): δ=0.98 (d, J=6.7 Hz, 6H), 2.01-2.10 (m, 1H), 3.57 (s, 2H), 3.68 (d, J=6.5 Hz, 2H), 7.17-7.19 (m, 2H).

Example 34: Preparation of Pimavanserin from Compound 2

To a 25 mL, three neck, round bottom flask, equipped with a stir bar, condenser and thermocouple, Compound 2, 0.210 g, was charged (FW: 249.26, 0.84 mmol, 1.0 equiv.). This was followed 3 mL of acetonitrile, anhydrous, 99.8%. The mixture was stirred at 60° C. for 4 h. Then, to the reaction mixture, Compound V, 0.375 g (FW: 222.30, 1.69 mmol, 2.0 equiv.), was added. After 1 h, complete conversion was observed. The reaction was diluted with EtOAc (20 mL) and washed twice with a saturated solution of NH4Cl (2×15 mL), then H2O (10 mL) and finally with a saturated NaCl solution (10 mL). The organic layer was dried over an h. sodium sulfate, filtered and concentrated under partial vacuum to about 5 mL of EtOAc. To this solution, n-heptane (10 ml) was added with vigorous stirring, in a dropwise manner, over half an hour. A white precipitate was formed, followed by filtration and drying in vacuum at 45° C. for 3 h, affording 0.188 g of Pimavanserin. HPLC-MS (m/z) [M+1]+ 428.2; 1H NMR (CDCl3, 400 MHz): δ=1.01 (d, J=6.7 Hz, 6H), 1.68-1.77 (m, 4H), 2.03-2.10 (m, 3H), 2.30 (s, 3H), 2.91-2.97 (m, 2H), 3.67 (d, J=6.7 Hz, 2H), 4.27 (d, J=5.4 Hz, 2H), 4.31-4.43 (m, 3H), 4.50 (brt, J=5.5 Hz, 1H), 6.74-6-79 (m, 2H), 6.95-7.05 (m, 4H), 7.14-7.22 (m, 2H).

Example 35: Preparation of N-(4-fluorobenzyl)-1-methylpiperidin-4-amine Dihydrochloride (Compound V×2HCl)

In a 100 mL round bottom flask, equipped with a stir bar, 4-fluorobenzylamine (10 mL, 0.088 mol) was dissolved in dry MeCN (110 mL), then 1-methylpiperidin-4-one (10.54 mL, 0.092 mol) was added and the reaction mixture was stirred at ambient temperature under N$_2$ atmosphere for 18 h to give the desired imine solution.

Reduction of the resulting imine was performed in a 250 mL reactor. Reactor was purged with N$_2$ and NaBH(OAc)$_3$ (29.84 g, 0.14 mol) was suspended in MeCN (80 mL). The suspension was cooled to 0-5° C. and solution of the imine in MeCN was added dropwise during 20 min. After the addition was completed, temperature was increased to 20° C. in 5° C. increments, during 1 h. After 2.5 h at 20° C., the reaction was quenched with addition of water (200 mL). Then DCM (100 mL) was added and pH was adjusted to 2 with 5M HCl solution. Layers were separated and aqueous one washed with DCM 2×100 mL, basified to pH 9.5 with 6M NaOH and extracted with DCM 2×100 mL. The combined organic layers were transferred to a 500 mL reactor and cooled to 10-15° C. To the resulting solution, 5-6 N HCl in 2-PrOH (3 equiv., 0.264 mmol) was added dropwise over 30 min. and white crystals were formed. The suspension was then cooled to 0-5° C. and stirred for 2 hours.

Crystals were filtered off, washed with 2×50 mL of DCM, dried at 50° C./10 mbar for 15 hours yielding 21.95 g (84.5%) of N-(4-fluorobenzyl)-1-methylpiperidin-4-amine dihydrochloride (Compound V×2HCl).

Example 36: Preparation of N-(4-fluorobenzyl)-1-methylpiperidin-4-amine dihydrochloride (Compound V×2HCl)

In a 50 mL three necked round bottom flask, equipped with a stir bar, thermometer and under N$_2$ atmosphere, 4-fluorobenzylamine (10 mL, 0.088 mol) was cooled to 0-5° C. and 1-methylpiperidin-4-one (12.2 mL, 0.106 mol) was added dropwise over 15 min. After the addition was completed, reaction mixture was stirred at 0-5° C. for additional 30 minutes to give the desired imine solution.

Reduction of the resulting imine was performed in a 500 mL three necked round bottom flask. The flask was purged with N$_2$ and NaBH$_4$ (5.32 g, 0.14 mol) was suspended in MeCN (50 mL). The suspension was cooled to 0-5° C. and solution of glacial acetic acid (24.1 mL, 0.42 mol) in MeCN (60 mL) was added dropwise over 60 minutes to give desired NaBH(OAc)$_3$. The solution of the imine in MeCN was then added dropwise into the suspension of in situ prepared NaBH(OAc)$_3$ at 0-5° C., over 30 min. After the addition was completed, reaction mixture was stirred at 0-5° C. for 1 hour and additionally 1.5 hours at 20° C. The reaction was quenched with addition of water (200 mL) and pH was adjusted to 2 with 5M HCl solution. After extraction with DCM (2×100 mL), layers were separated and aqueous one was basified to pH 9.5 with 6M NaOH and extracted with DCM (2×100 mL). The combined organic layers were transferred to a 500 mL three necked round bottom flask and cooled to 0-5° C. To the resulting solution, 5-6 N HCl in 2-PrOH (3 equiv., 0.264 mmol) was added dropwise over 10 min. and white crystals were formed. The suspension was stirred at 0-5° C. for 1 hour.

Crystals were filtered off, washed with 2×50 mL of DCM, dried at 45° C./10 mbar for 10 hours yielding 21.62 g (83.3%) of N-(4-fluorobenzyl)-1-methylpiperidin-4-amine dihydrochloride (Compound V×2HCl).

Example 37: Preparation of N-(4-fluorobenzyl)-1-methylpiperidin-4-amine dihydrochloride (Compound V×2HCl)

In a 100 mL three round bottom flask, equipped with a stir bar, thermometer and under N₂ atmosphere, 4-fluorobenzylamine (10 mL, 0.088 mol) was cooled to 0-5° C. and 1-methylpiperidin-4-one (12.05 mL, 0.106 mol) was added dropwise over 20 min. After the addition was completed, temperature was increased to ambient temperature and stirred for next 2 h.

Reduction of the resulting imine was performed in a 600 mL autoclave with addition of Raney-Ni (3.3 g, 30 wt. %), glacial acetic acid (5.03 mL, 0.088 mol), MeOH (75 mL) and at 5 bar pressure for 66 h. After filtration of catalyst through Celite, the solution was concentrated to 50 mL and water (100 mL) and DCM (100 mL) were added. pH of this solution was adjusted to 2 with 5M HCl. Layers were separated and aqueous one washed with once again with DCM (100 mL), basified to pH 9.5 with 6M NaOH and extracted with DCM 2×100 mL. The combined organic layers were transferred to a 500 mL reactor and cooled to 10-15° C. To the resulting solution, 5-6 N HCl in 2-PrOH (3 equiv., 0.264 mol) was added dropwise over 30 min. and white crystals were formed. The suspension was then cooled to 0-5° C. and stirred for 2 hours.

Crystals were filtered off, washed with 2×50 mL of DCM, dried at 50° C./10 mbar for 15 hours yielding 22.05 g (84.9%) of N-(4-fluorobenzyl)-1-methylpiperidin-4-amine dihydrochloride (Compound V×2HCl).

Example 38: Preparation of Pimavanserin from Compound and Compound V×2HCl 250 mL reactor was charged with N-hydroxy-2-(4-isobutoxyphenyl)acetamide (Compound 1) (10 g, 0.045 mol), CDI (10.53 g, 0.076 mol) and 100 mL of MeCN, p.a. The resulting solution was stirred for 1.5 h at 60-65° C. and monitored by HPLC. Upon full conversion to the corresponding isocyanate, reaction solution was cooled to 35° C. and N-(4-fluorobenzyl)-1-methylpiperidin-4-amine dihydrochloride (Compound V×2HCl) (22.48 g, 0.065 mol) and K₂CO₃ (6.19 g, 0.045 mol) were added. Reaction mixture was heated up to 60-65° C. and stirred for 6 hours and followed by 17 h at ambient temperature.

Upon completion, the reaction solution was cooled to 20° C. and water was added dropwise in ratio 1:3 (300 mL) with adjustment of pH to 11 with 6N NaOH solution. After addition of whole amount of water, crystals were formed and suspension was stirred at 20° C. for 2 h and 0-5° C. for next 2 hour. Crystals were filtered off, washed with 2×100 mL solution of MeCN:H₂O 1:3, then 100 mL of H₂O, dried at 30° C./10 mbar for 24 hours yielding 17.56 g (91.7%) of Pimavanserin.

The invention claimed is:
1. A compound of formula (XVII), (Z), or (XIX):

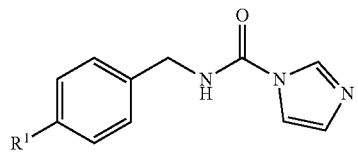

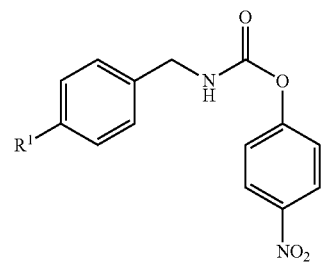

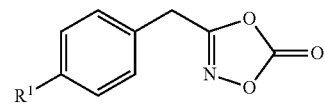

wherein:
R¹ is a 2-methylpropan-oxy ("isobutoxy") group or a group that can be converted into an isobutoxy group.
2. The compound of formula (XVII) of claim 1, that is:

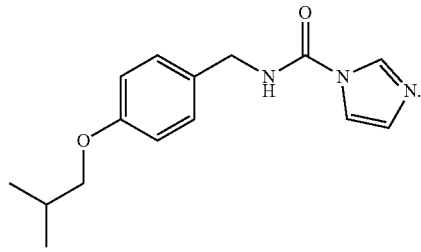 [SMILES: CC(C)COc1ccc(CNC(=O)n2ccnc2)cc1]

3. The compound of formula (Z) of claim 1, that is:

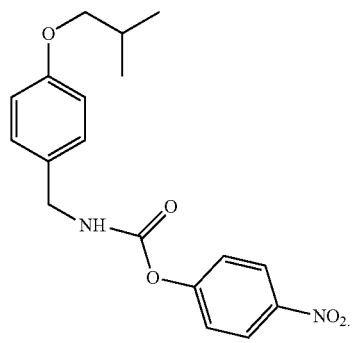 [SMILES: CC(C)COc1ccc(CNC(=O)Oc2ccc([N+](=O)[O-])cc2)cc1]

4. The compound of formula (XIX) of claim 1, wherein R¹ is 2-methylpropan-oxy.

* * * * *